(12) United States Patent
Pancholy

(10) Patent No.: US 10,716,576 B2
(45) Date of Patent: *Jul. 21, 2020

(54) METHOD TO STOP BLEEDING, WITH SHORT HEMOSTASIS DURATION USING A LOW DOSE OF ANTICOAGULANT

(71) Applicant: Samir Bipin Pancholy, Clarks Summit, PA (US)

(72) Inventor: Samir Bipin Pancholy, Clarks Summit, PA (US)

(73) Assignee: VASOINNOVATIONS INC., South Pasadena, CA (US)

( * ) Notice: Subject to any disclaimer, the term of this patent is extended or adjusted under 35 U.S.C. 154(b) by 78 days.

This patent is subject to a terminal disclaimer.

(21) Appl. No.: 16/255,834

(22) Filed: Jan. 24, 2019

(65) Prior Publication Data

US 2019/0150941 A1   May 23, 2019

Related U.S. Application Data

(63) Continuation of application No. 16/138,958, filed on Sep. 21, 2018, now Pat. No. 10,213,214, and a
(Continued)

(51) Int. Cl.
*A61B 17/135* (2006.01)
*A61B 17/132* (2006.01)
*A61B 17/12* (2006.01)

(52) U.S. Cl.
CPC .......... *A61B 17/1325* (2013.01); *A61B 17/12* (2013.01); *A61B 17/135* (2013.01); *A61B 2017/12004* (2013.01)

(58) Field of Classification Search
CPC . A61B 17/1285; A61B 17/132; A61B 17/135; A61B 17/1322
(Continued)

(56) References Cited

U.S. PATENT DOCUMENTS 37,156 A    12/1862 Dunton
3,905,361 A   9/1975 Hewson et al.
(Continued)

FOREIGN PATENT DOCUMENTS

EP    0 601 756 A1    6/1994
EP    1 382 306 A2    1/2004
(Continued)

OTHER PUBLICATIONS

Pancholy et al "Comparison of a Priori Versus Provisional Heparin Therapy on Radial Artery Occlusion After Transradial CoronaryAngiography and Patent Hemostasis (from the PHARAOH Study)" Am J Cardiol, 110:173-176 (Year: 2012).*
(Continued)

*Primary Examiner* — Elizabeth Houston
*Assistant Examiner* — Socrates L Boutsikaris
(74) *Attorney, Agent, or Firm* — Rajendra G. Sardesai

(57) ABSTRACT

Disclosed are methods and devices for obtaining patent hemostasis of the radial artery by compressing the uninstrumented ulnar artery to increase radial artery flow. The device comprises a band having an inflatable bladder for applying blunt pressure to the ulnar artery. The method comprises applying a pressure to the homolateral ulnar artery and applying a pressure to the radial artery at the access site to obtain hemostasis at the access site.

18 Claims, 16 Drawing Sheets

Related U.S. Application Data continuation-in-part of application No. 15/708,123, filed on Sep. 18, 2017, now Pat. No. 10,342,551, which is a continuation-in-part of application No. 15/426,056, filed on Feb. 7, 2017, now Pat. No. 9,949,738, which is a continuation-in-part of application No. 15/340,023, filed on Nov. 1, 2016, now Pat. No. 9,592,060, which is a continuation of application No. 15/062,150, filed on Mar. 6, 2016, now Pat. No. 9,510,838, which is a continuation of application No. 13/941,219, filed on Jul. 12, 2013, now Pat. No. 9,308,000.

(60) Provisional application No. 62/653,172, filed on Apr. 5, 2018, provisional application No. 62/549,923, filed on Aug. 24, 2017, provisional application No. 62/405,951, filed on Oct. 9, 2016.

(58) Field of Classification Search
USPC .............. 606/201–203; 601/132, 151, 33, 40
See application file for complete search history.

(56) References Cited

U.S. PATENT DOCUMENTS

| | | |
|---|---|---|
| 4,469,099 A | 9/1984 | McEwen |
| 4,863,429 A | 9/1989 | Baldwin |
| 4,920,971 A | 5/1990 | Blessinger |
| 4,981,133 A | 1/1991 | Rollband |
| 5,152,302 A | 10/1992 | Fareed |
| 5,295,951 A | 3/1994 | Fareed |
| 5,307,811 A | 5/1994 | Sigwart et al. |
| 5,413,582 A | 5/1995 | Eaton |
| 5,433,724 A | 7/1995 | Kawasaki et al. |
| 5,464,420 A | 11/1995 | Hori et al. |
| 5,486,194 A | 1/1996 | Kawasaki et al. |
| 5,496,262 A | 3/1996 | Johnson et al. |
| 5,514,155 A | 5/1996 | Daneshvar |
| 5,569,297 A | 10/1996 | Makower et al. |
| 5,643,315 A | 7/1997 | Daneshvar |
| 5,660,182 A | 8/1997 | Kuroshaki et al. |
| 5,690,610 A | 11/1997 | Ito et al. |
| 5,779,657 A | 7/1998 | Daneshvar |
| 5,792,173 A | 8/1998 | Breen et al. |
| 5,840,037 A | 11/1998 | Tochikubo et al. |
| 6,007,562 A | 12/1999 | Harren et al. |
| 6,336,901 B1 | 1/2002 | Itonaga et al. |
| 6,361,496 B1 | 3/2002 | Zikorus et al. |
| 6,527,727 B2 | 3/2003 | Itonaga et al. |
| 6,694,821 B2 | 2/2004 | Yamakoshi et al. |
| 6,827,727 B2 | 12/2004 | Stalemark et al. |
| 7,498,477 B2 | 3/2009 | Wada et al. |
| 7,927,295 B2 | 4/2011 | Bates et al. |
| 8,034,009 B2 | 10/2011 | Bates et al. |
| 8,152,776 B2 | 4/2012 | McCluskey |
| 8,481,803 B2 | 7/2013 | Wada et al. |
| 8,481,805 B2 | 7/2013 | Wada et al. |
| 8,524,974 B2 | 9/2013 | Wada et al. |
| 8,759,603 B2 | 6/2014 | Wada et al. |
| 8,895,155 B2 | 2/2018 | Wada et al. |
| 2002/0115603 A1 | 8/2002 | Whitehouse |
| 2002/0147404 A1 | 10/2002 | Kato |
| 2002/0170359 A1 | 11/2002 | Yamakoshi et al. |
| 2003/0199922 A1 | 10/2003 | Buckman |
| 2004/0049214 A1 | 3/2004 | Akerfeldt |
| 2004/0098035 A1 | 5/2004 | Wada |
| 2004/0122469 A1 | 6/2004 | Akerfeldt |
| 2004/0193059 A1 | 9/2004 | Inoue et al. |
| 2005/0153090 A1 | 7/2005 | Marchitto |
| 2006/0149153 A1 | 7/2006 | Shirasaki et al. |
| 2009/0138039 A1 | 5/2009 | Wada et al. |
| 2009/0234261 A1 | 9/2009 | Singh |
| 2009/0281565 A1 | 11/2009 | McNeese |
| 2010/0179586 A1 | 7/2010 | Ward et al. |
| 2012/0071804 A1 | 3/2012 | Philip et al. |
| 2012/0296369 A1 | 11/2012 | Atthoff et al. |
| 2013/0116725 A1 | 5/2013 | Wada et al. |
| 2013/0178894 A1 | 7/2013 | Wada et al. |
| 2013/0237866 A1 | 9/2013 | Cohen |
| 2013/0245674 A1 | 9/2013 | Wada et al. |
| 2013/0245675 A1 | 9/2013 | Wada et al. |
| 2013/0282048 A1 | 10/2013 | Wada et al. |
| 2013/0289613 A1 | 10/2013 | Wada et al. |
| 2014/0142615 A1 | 5/2014 | Corrigan, Jr. |
| 2015/0018869 A1* | 1/2015 | Benz ................... A61B 17/135 606/203 |
| 2015/0201948 A1 | 7/2015 | Kornowski et al. |
| 2016/0174952 A1 | 7/2016 | Shah |
| 2016/0213373 A1 | 7/2016 | Drasler et al. |
| 2016/0338709 A1 | 11/2016 | Wada et al. |
| 2018/0000491 A1 | 1/2018 | Wada et al. |
| 2018/0000492 A1 | 1/2018 | Wada et al. |
| 2018/0000493 A1 | 1/2018 | Wada et al. |
| 2018/0000494 A1 | 1/2018 | Wada et al. |
| 2018/0014833 A1 | 1/2018 | Wada et al. |

FOREIGN PATENT DOCUMENTS

| | | |
|---|---|---|
| EP | 2 070 483 A2 | 6/2009 |
| EP | 2 245 998 A1 | 11/2010 |
| GB | 2486194 A | 6/2012 |
| JP | 56-33526 Y2 | 8/1981 |
| JP | 5-305093 A | 11/1993 |
| JP | 7-79983 A | 3/1995 |
| JP | 8-71077 A | 3/1996 |
| JP | 8-140990 A | 6/1996 |
| JP | 3031486 U | 9/1996 |
| JP | 10-57386 A | 3/1998 |
| JP | 2000-515773 A | 11/2000 |
| SG | 178650 A1 | 3/2012 |
| WO | WO 97/02783 A1 | 1/1997 |
| WO | WO-97/17900 A1 | 5/1997 |
| WO | WO-2012/126154 A1 | 9/2012 |

OTHER PUBLICATIONS

U.S. Appl. No. 13/941,219, filed Jul. 12, 2013, now U.S. Pat. No. 9,308,000.
U.S. Appl. No. 14/819,383, filed Aug. 5, 2015, now U.S. Pat. No. 9,332,994.
U.S. Appl. No. 15/062,150, filed Mar. 6, 2016, now U.S. Pat. No. 9,510,838.
U.S. Appl. No. 15/093,739, filed Apr. 8, 2016, now U.S. Pat. No. 9,408,611.
U.S. Appl. No. 15/099,603, filed Apr. 15, 2016, now U.S. Pat. No. 9,642,628.
U.S. Appl. No. 15/150,394, filed May 9, 2016, now U.S. Pat. No. 9,668,744.
U.S. Appl. No. 15/340,023, filed Nov. 1, 2016, now U.S. Pat. No. 9,592,060.
U.S. Appl. No. 15/417,480, filed Jan. 27, 2017, now U.S. Pat. No. 10,213,212.
U.S. Appl. No. 15/426,056, filed Feb. 7, 2017, now U.S. Pat. No. 9,949,738.
U.S. Appl. No. 15/487,661, filed Apr. 14, 2017, now U.S. Pat. No. 10,213,213.
U.S. Appl. No. 15/588,586, filed May 5, 2017, now U.S. Pat. No. 10,335,161.
U.S. Appl. No. 15/630,920, filed Jun. 22, 2017, now U.S. Pat. No. 10,349,951.
U.S. Appl. No. 15/708,123, filed Sep. 18, 2017, now U.S. Pat. No. 10,342,551.
U.S. Appl. No. 15/898,591, filed Feb. 18, 2018, now U.S. Pat. No. 10,117,672.
U.S. Appl. No. 15/924,273, filed Mar. 18, 2018.
U.S. Appl. No. 16/056,261, filed Aug. 6, 2018, now U.S. Pat. No. 10,357,254.
U.S. Appl. No. 16/130,201, filed Sep. 13, 2018.

(56) References Cited

OTHER PUBLICATIONS

U.S. Appl. No. 16/130,959, filed Sep. 13, 2018, now U.S. Pat. No. 10,507,026.
U.S. Appl. No. 16/134,091, filed Sep. 18, 2018, now U.S. Pat. No. 10,342,545.
U.S. Appl. No. 16/136,913, filed Sep. 20, 2018, now U.S. Pat. No. 10,245,041.
U.S. Appl. No. 16/138,958, filed Sep. 21, 2018, now U.S. Pat. No. 10,213,214.
U.S. Appl. No. 16/179,044, filed Nov. 2, 2018.
U.S. Appl. No. 16/252,725, filed Jan. 21, 2019.
U.S. Appl. No. 16/254,589, filed Jan. 23, 2019.
U.S. Appl. No. 16/281,129, filed Feb. 21, 2019.
Examiner's Search in priority U.S. Appl. No. 13/941,219, filed Jul. 12, 2013—Other References Patent.
Examiner's Search in priority U.S. Appl. No. 13/941,219, filed Jul. 12, 2013—Other References NPL.
Examiner's Search in priority U.S. Appl. No. 13/941,219, filed Jul. 12, 2013—Other References Inventor.
U.S. Appl. No. 13/933,025, filed Jul. 1, 2013, Wada et al.
U.S. Appl. No. 13/889,101, filed May 7, 2013, Wada et al.
U.S. Appl. No. 13/889,112, filed May 7, 2013, Wada et al.
U.S. Appl. No. 15/229,455, filed Aug. 5, 2016, Wada et al.
U.S. Appl. No. 15/705,483, filed Sep. 15, 2017, Wada et al.
U.S. Appl. No. 15/705,570, filed Sep. 15, 2017, Wada et al.
U.S. Appl. No. 15/705,994, filed Sep. 15, 2017, Wada et al.
U.S. Appl. No. 15/706,301, filed Sep. 15, 2017, Wada et al.
U.S. Appl. No. 15/706,397, filed Sep. 15, 2017, Wada et al.
Patel, T. et al, "Balloon-assisted tracking: A must-know technique . . . " Cath. Cardio. Interv., Wileyonlinelibrary.com; DOI:10.1002/ccd.24959, Apr. 2013.
Kwan, T. et al, "Transulnar catheterization in patients with ipsilateral radial artery occlusion" Cath Cardio Interv, Wileyonlinelibrary.com, DOI 10.1002/ccd.24662 Sep. 2012.
Patel, T. et al, "Balloon-assisted tracking of a guide catheter . . . : A technical report" Cath. Cardio. Interv., Wileyonlinelibrary.com; DOI 10.1002/ccd.24504, May 2012.
Kwan, T. et al. "Feasibility and safety of 7F sheathless guiding catheter during transradial coronary intervention", Wileyonlinelibrary.com; DOI 10.1002/ccd.24310, Aug. 2012.
Pancholy, S et al, "Comparison of a priori versus provisional heparin therapy on radial artery occlusion . . . (PHARAOH Study)", Am J Cardiol, vol. 110(2), p. 173-176 Jul. 2012.
Pancholy, S et al, "Radial artery access technique evaluation trial: randomized comparison . . . ", Catheter Cardiovasc Interv., vol. 80(2), p. 288-91, Aug. 2012.
Pancholy, S et al, "Effect of duration of hemostatic compression on radial artery occlusion after transradial access", Catheter Cardio Interv, vol. 79(1), p. 78-81, Jan. 2012.
Caputo, R, et al, "Transradial arterial access for coronary and peripheral procedures . . . " Catheter Cardiovasc Interv., vol. 78(6), p. 823-39, Nov. 2011.
Bertrand, O et al, "Transradial approach for coronary angiography and interventions . . . ", JACC Cardiovasc Interv., vol. 3(10), p. 1022-31 Oct. 2010.
Pancholy, S et al, "Comparison of door-to-balloon times for primary PCI using transradial versus transfemoral approach" Catheter Cardio Interv. vol. 75(7), p. 991-5 Jun. 2010.
Pancholy, S et al "A technique to access difficult to find upper extremity veins for right heart catheterization . . . " Catheter Cardiovasc Interv., 78(5):809-12, Nov. 2011.
Patel, T et al, "Reaccessing an occluded radial artery: a "proximal entry" technique" J Interv Cardiol. 24(4):378-81, Aug. 2011.
Patel, T et al, "Management of radial and brachial artery perforations during transradial procedures . . . " J Invasive Cardiol. 21(10):544-7, Oct. 2009.
Patel, T et al, "A simple approach for the reduction of knotted coronary catheter in radial artery during transradial approach" J Invasive Cardiol. 23(5):E126-7, May 2011.
Pancholy, S. et al Prevention of radial artery occulusion . . . , The PROPHET-II Randomized trial, JACC: Cardiovascular Interventions, vol. 9 (19), pp. 1992-1999, Oct. 2016.
Maden, O. et al "Relation between end-procedural activated clotting time values . . . after transradial catheterization" Am. J. Cardiol., vol. 118, pp. 1455-1459 (2016).
Hahalis, G. et al "A comparison of low versus standard heparin dose . . . after 5 French coronary angiography" Int. J. Cardiol. vol. 187, pp. 404-410 (2015).
Aykan, A. et al "Comparison of low dose versus standard dose heparin for radial approach in elective coronary angiography" Int. J. Cardiol. vol. 187, pp. 389-392 (2015).
Uhlemann, M. et al. "The leipzig prospective vascular ultrasound registry in radial artery catheterization", JACC: Cardiovascular Interventions, vol. 5, No. 1, pp. 36-43 (2012).
Roghani, R. et al. "The effect of low dose versus standard dose of arterial heparin . . . randomized clinical trial", ARYA Atheroscler, vol. 12 (1), pp. 10-17 (2016).
Kiemeneij, F. et al. "The PROPHET-II's Prophecy", JACC: Cardiovascular Interventions, vol. 9, No. 19, pp. 2000-2001, Oct. 2016.
Extended European Search Report Application No. EP 18163282.
Letter regarding Commonly Assigned Copending and Allowed Applications.
Extended European Search Report Application No. EP 16833489.
International Search Report in International application No. PCT/US 16/45207.
Written Opinion of the International Searching Authority in International application No. PCT/US 16/45207.
European Search Report Application No. EP 16181506.
International Preliminary Report on Patentability (Chapter 1 of PCT) International Application No. PCT/US2016/041801.
International Preliminary Report on Patentability (Chapter 1 of PCT) International Application No. PCT/US2016/045207.
Patel, T. et al, "Contralateral transradial approach for carotid artery stenting: a feasibility study" J. Catheter Cardiovasc Interv. vol. 75(2), p. 268-75. Feb. 2010.
Pancholy, S. "Comparison of the effect of intra-arterial versus intravenous heparin on radial artery occlusion . . . " Am J Cardiol. vol. 104(8) p. 1083-5 Oct. 2009.
Pancholy, S. "Prevention of Radial Artery Occlusion:Prophylactic Hyperperfusion Evaluation Trial ( PROPHET-II)" ClinicalTrial. Gov, Protocol Registration System, Mar. 2012.
Pancholy, S. et al, "Subcutaneous administration of nitroglycerin to facilitate radial artery cannulation" Catheter Cardiovasc Interv. vol. 68(3) p. 389-9, Sep. 2006.
Mamas, M, "Dissection, Occlusion, and Spasm; Myths Involving Sheathless Guide Catheters" Catheterization and Cardiovascular Interventions 76:777-778, Feb. 2010.
Pancholy, S "Hemostasis and Radial Artery Patency", Presentation, http://www.slideshare.net/theradialist/pancholy-sb-201111, Jan. 2012.
Shroff, A et al "Comparing radial with femoral artery access in patients with ST-segment elevation myocardial infarction . . . " Expert Rev Cardio Ther. 11(5):525-7, May 2013.
Patel, T et al "Coronary cannulation through mirror-image right aortic arch during right transradial approach . . . " J Invasive Cardiol. 24(5):234-5, May 2012.
Kwan, T. et al "Balloon-assisted sheathless transradial intervention (BASTI) using 5 Fr guiding catheters" J Invasive Cardiol. 24(5):231-3, May 2012.
Dharma, S. et al "Nitroglycerin plus diltiazem versus nitroglycerin alone for spasm prophylaxis with transradial approach" J Invasive Cardiol. 24(3):122-5, Mar. 2012.
International Search Report in International application No. PCT/US 16/41801.
Written Opinion of the International Searching Authority in International application No. PCT/US 16/41801.
Search History in International application No. PCT/US 1641801.
Samir Pancholy, et al, "Prevention of Radial Artery Occlusion—Patent Hemostasis Evaluation Trial (PROPHET study)" Catheterization and Cardiovascular Interv 72:335-340 (2008).
Samir B. Pancholy, "Transradial Access in an Occluded Radial Artery: New Technique" Journal Invasive Cardiology, vol. 19, Issue 12, Dec. 2007.

(56) References Cited

OTHER PUBLICATIONS

Samir B. Pancholy, "Transradial Approach" Angioplasty.Org Interview Series, 3 pages, Aug. 2008.
Samir B. Pancholy, "Impact of Two Different Hemostatic Devices on Radial Artery Outcomes after Transradial Catheterization" J Invasive Cardiology, vol. 21, Issue 3, Mar. 2009.
Ivo Bernat, et al, "Efficacy and Safety of Transient Ulnar Artery Compression to Recanalize Actute Radial Artery Occlusion . . . " Am J Cardiol, 107:1698-1701(2011).
Samir B. Pancholy, "Strategies to Prevent Radial Artery Occlusion After Transradial PCI" Curr Cardiol Rep, 16:505, Jun. 2014.

* cited by examiner

METHOD TO STOP BLEEDING, WITH SHORT HEMOSTASIS DURATION USING A LOW DOSE OF ANTICOAGULANT

CROSS-REFERENCE TO RELATED APPLICATIONS

This application is a continuation of co-pending U.S. patent application Ser. No. 16/138,958 filed Sep. 21, 2018, which is a non-provisional of U.S. Provisional Application No. 62/653,172 filed Apr. 5, 2018 and continuation-in-part of co-pending U.S. patent application Ser. No. 15/708,123, filed Sep. 18, 2017, which is non-provisional of U.S. Provisional Application No. 62/549,923 filed Aug. 24, 2017 and is a continuation-in-part of U.S. patent application Ser. No. 15/426,056, filed Feb. 7, 2017, now U.S. Pat. No. 9,949,738, issued Apr. 24, 2018, which is non-provisional of U.S. Provisional Application No. 62/405,951 filed Oct. 9, 2016 and is a continuation-in-part of U.S. patent application Ser. No. 15/340,023, filed Nov. 1, 2016, now U.S. Pat. No. 9,592,060 issued Mar. 14, 2017, which is a continuation of U.S. patent application Ser. No. 15/062,150, filed Mar. 6, 2016, now U.S. Pat. No. 9,510,838 issued Dec. 6, 2016, which is a continuation of U.S. patent application Ser. No. 13/941,219, filed Jul. 12, 2013, now U.S. Pat. No. 9,308,000 issued Apr. 12, 2016.

The entire content of all above applications is incorporated herein by reference.

BACKGROUND OF INVENTION a. Field of Invention

The invention relates generally to transradial catheterization methods and devices used in said methods. In particular the invention concerns a method of obtaining patent hemostasis of the radial artery by compressing the un-instrumented ulnar artery to increase radial artery flow while applying pressure to the radial artery access site. The invention further concerns a device for applying blunt pressure to the ulnar artery, and a method of use.

b. Description of Related Art

Radial artery instrumentation is becoming increasingly prevalent with cardiovascular procedures performed via transradial access, providing improvement in outcomes, cost, as well as comfort. Radial artery occlusion refers to the blockage of the radial artery. Radial artery occlusion is a consequence of radial artery cannulation, which obliterates the radial artery lumen, making it not available for access in the future.

After instrumentation, it is necessary to compress the radial artery at the access site to obtain hemostasis of the cannulation wound. The cannulation wound is an opening of the wall of the radial artery. Hemostasis of the cannulation (or sheath) wound is accomplished by applying blunt pressure to the radial artery at the cannulation wound site, or access site. The application of this blunt pressure on the radial artery often causes the artery to occlude or close, thereby denying bloodflow further downstream within the radial artery. Maintaining blood flow in the radial artery while compressing the access site, after instrumentation, reduces the risk of post-instrumentation radial artery occlusion. Patent hemostasis is therefore understood to mean achieving the cessation of bleeding at the cannulation wound (access site) of the radial artery, while blood is allowed to flow through the artery.

The following references are representative of the field pertaining to the present invention:

For example, U.S. Pat. No. 6,355,026 to Mick describes right and left coronary catheters that are designed to be used in a transradial coronary catheterization. Also discussed are methods of inserting the catheters into a right or left coronary artery by a transradial approach.

In an article entitled Efficacy and Safety of Transient Ulnar Artery Compression to Recanalize Acute Radial Artery Occlusion After Transradial Catheterization (Am J Cardiol 2011; 107:1698-1701) Ivo Bernat, MD, and others, discuss a method directed to open an occluded radial artery after the radial artery becomes occluded. In the case of radial artery occlusion, 3-4 hours after hemostasis of the radial artery, ulnar artery compression was applied to attempt recanalization of radial artery. Bernat et. al. verified reopening of the radial artery by administration of heparin and compression of the ulnar artery.

Transradial access is being increasingly used because of its ability to reduce access-site complications and increase patient comfort. While performing transradial catheterization, upon introduction of the introducer sheath or catheter into the radial artery, it is best practice to administer anticoagulant, e.g., unfractionated heparin, bivalirudin or Enoxaparin, to assist in the prevention of radial artery occlusion, even when the catheterization procedure itself would otherwise not require it. Anticoagulants may also be referred to as blood thinners. The prophylactic effect of an anticoagulant such as unfractionated heparin to reduce the occurrence of radial artery occlusion is dose-dependent with significantly better efficacy with higher doses. With the administration of 5000 units of unfractionated heparin or alternatively 50 units per kilogram (kg) of body weight, radial artery occlusion rates have been reported in the range of 4-5%. Doses of heparin to be administered are generally expressed in units of heparin per kg of body weight. A conventional dose of unfractionated heparin during a transradial catheterization procedure is about 50 units per kg of body weight. A conventional dose of other anticoagulants, such as Bivalirudin or Enoxaparin is the equivalent of 50 units of unfractionated heparin per kg of body weight.

In view of the anticoagulant effect of unfractionated heparin, which effect typically exceeds the duration of the cardiovascular procedure, the patient is systemically anticoagulated with observed activated clotting times of approximately 200-225 seconds, while undergoing hemostasis. Optimally, a minimum duration of about 120 minutes of compression at the radial artery access site is required to achieve hemostasis.

SUMMARY OF INVENTION

A present invention method of catheterization of the radial artery directed at minimizing occurrences of radial artery occlusion is disclosed. The method comprises inserting a sheath into the radial artery of a patient at an access site. The desired catheterization procedure is then performed using the sheath to access the radial artery. Once the catheterization procedure is complete, an ulnar pressure is applied to the homolateral ulnar artery at an ulnar pressure site while the sheath remains inserted in the radial artery. The sheath is then removed from the radial artery while maintaining the ulnar pressure to the ulnar artery. Once the sheath is removed, and while continuing to apply the ulnar pressure, pressure is applied to the radial artery at the access site to obtain hemostasis at the access site.

In a preferred embodiment, the step of "applying a pressure to the radial artery at the access site to obtain hemostasis at the access site" is accomplished while maintaining the ulnar pressure to the ulnar artery.

In an embodiment of the present invention, a further step includes confirming that the step of applying ulnar pressure has reduced blood flow through the ulnar artery by monitoring flow of the ulnar artery prior to and after applying the ulnar pressure. In a further embodiment, monitoring flow of the ulnar artery includes sensing skin blood flow and/or pulsation at a fingertip or other location downstream of the ulnar pressure site. Digital plethysmography is employed in a preferred embodiment.

In another embodiment, the method further includes confirming patency of the radial artery during the step of applying a pressure to the radial artery by sensing skin blood flow and/or pulsation at a fingertip or other location downstream of the access site. In this embodiment, the sensing is performed while the ulnar artery is fully compressed (allowing no flow through the ulnar artery) and/or partially compressed (allowing less flow than when not compressed at all). Patency is confirmed, in an embodiment, by obtaining a metric relating to the sensing and comparing the metric with a standard metric for the patient, or with a previously-sensed metric. Preferably, the previously sensed metric is read after the applying the ulnar pressure step and before the step of removing the sheath from the radial artery. Digital plethysmography is employed in a preferred embodiment. In yet another embodiment, the method further includes administering anticoagulant at a dose lower than a conventional dose when an increased flow of blood is provided in the artery that is punctured at the access site.

In an embodiment of the present invention method, the step of compressing the ulnar artery includes: providing an ulnar impinger, securing the ulnar impinger over the wrist such that the impinger contacts a first location over the ulnar artery, and activating the impinger to press on the ulnar artery at the first location.

In a preferred embodiment of the present invention, the step of compressing the ulnar artery includes: providing an ulnar impingement band having an inflatable bladder, securing the ulnar impingement band over the wrist such that the bladder contacts a first location over the ulnar artery, and inflating the bladder to impinge upon the ulnar artery at the first location.

There is further disclosed a device for use in applying a compressing force to the ulnar artery of a patient. The device includes a trunk having an inflatable bladder. The trunk is defined by a lower portion and an upper portion. The bladder is defined by an expandable envelopment existing between the lower portion and the upper portion. A pair of limbs are connected to and extend from the upper portion of the trunk. Together, the pair of limbs and the trunk form a general Y-shape. A first limb of the pair of limbs is adapted to lay across the palm of a hand, between the thumb and the index finger and connect to the trunk to secure the first limb to the trunk and to secure the bladder to a portion of the patient's wrist corresponding with a first location over the ulnar artery. A second limb of the pair of limbs is adapted to lay over the wrist/distal forearm and connect to the trunk. This is to secure the second limb to the trunk and to further secure the bladder to the first location over the ulnar artery. One or more connectors are utilized for fixing the pair of limbs to the trunk.

In use, the bladder is located at the first location over the ulnar artery, and the pair of limbs are fixed around the hand and wrist to the trunk with the connectors. The bladder is inflated with a tube connected to an inflator to cause the bladder to impinge upon the ulnar artery at the first location.

There is further disclosed a device for use in applying a compressing force to the ulnar artery of a patient. The device comprises a trunk having an impinger. The trunk is defined by a lower portion and an upper portion. The impinger is defined by any device sufficient to apply a compression force. A pair of limbs are connected to and extend from the upper portion of the trunk. The pair of limbs together with the trunk form a general Y-shape. A first limb of the pair of limbs is adapted to lay across the palm of a hand, between the thumb and the index finger. The first limb connects to the trunk to secure the first limb to the trunk, and also to secure the impinger to a portion of the patient's wrist corresponding with a first location over the ulnar artery. A second limb of the pair of limbs is adapted to lay over the wrist/distal forearm and connect to the trunk to secure the second limb to the trunk and to further secure the bladder to the first location over the ulnar artery. One or more connectors are employed to fix the pair of limbs to the trunk. In use, the impinger is located at the first location over the ulnar artery. The pair of limbs are fixed around the hand and wrist to the trunk with the connectors. The impinger is activated to cause the bladder to impinge upon the ulnar artery at the first location.

Additional features, advantages, and embodiments of the invention may be set forth or are apparent from consideration of the following detailed description, drawings, and claims. Moreover, it is to be understood that both the foregoing summary of the invention and the following detailed description are exemplary and intended to provide further explanation without limiting the scope of the invention as claimed.

BRIEF DESCRIPTION OF THE DRAWINGS

The accompanying drawings, which are included to provide a further understanding of the invention and are incorporated in and constitute a part of this specification, illustrate preferred embodiments of the invention and together with the detailed description serve to explain the principles of the invention. In the drawings.

DETAILED DESCRIPTION OF THE EMBODIMENTS

The invention is directed to a method of obtaining patent hemostasis of the radial artery by compressing the un-instrumented ulnar artery to increase radial artery flow while applying pressure to the radial artery access site. The invention further concerns a device for applying blunt pressure to the ulnar artery, and a method of use.

Figure 1:
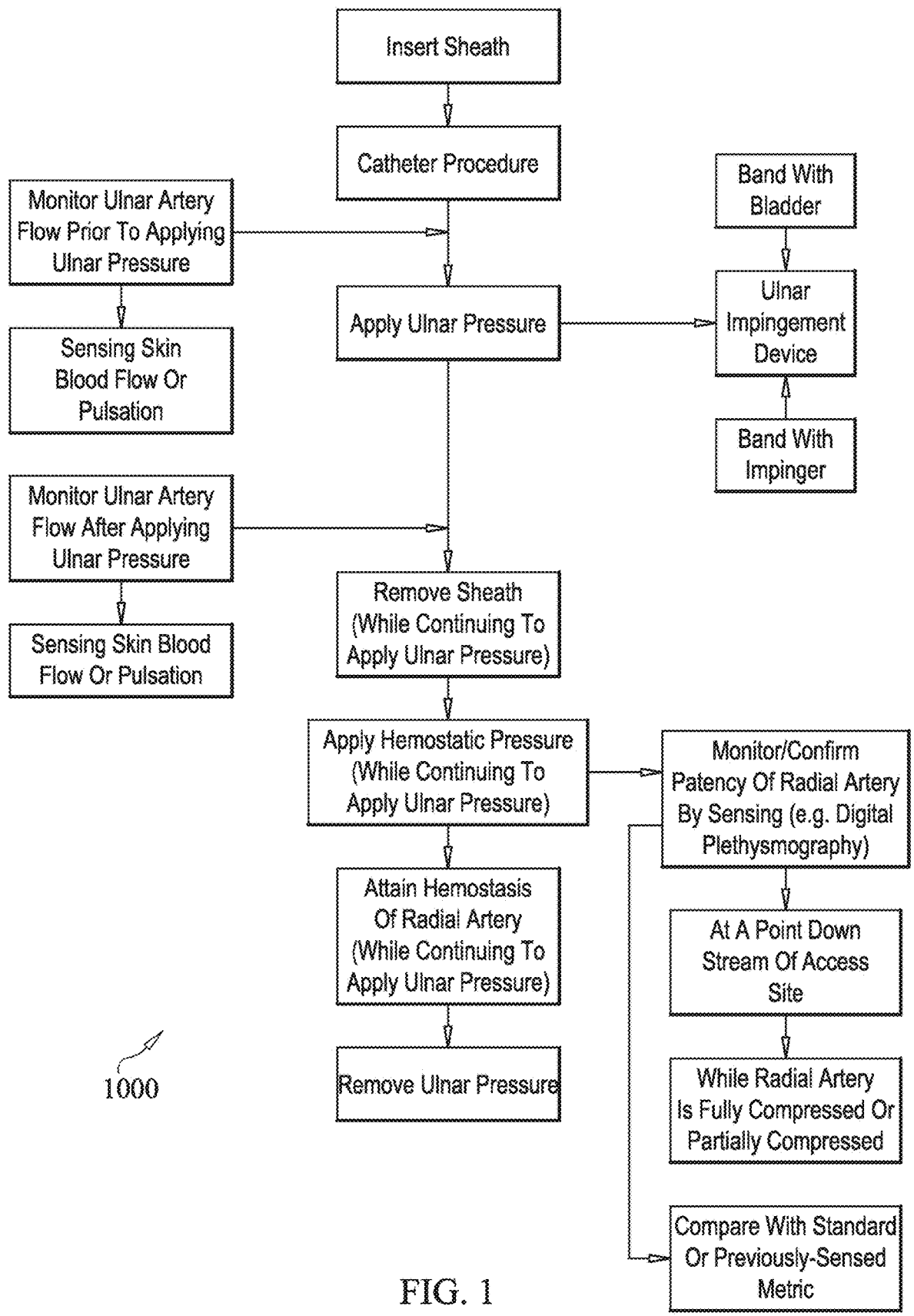
FIG. 1 is schematic layout of methods disclosed herein.
Figure 2:
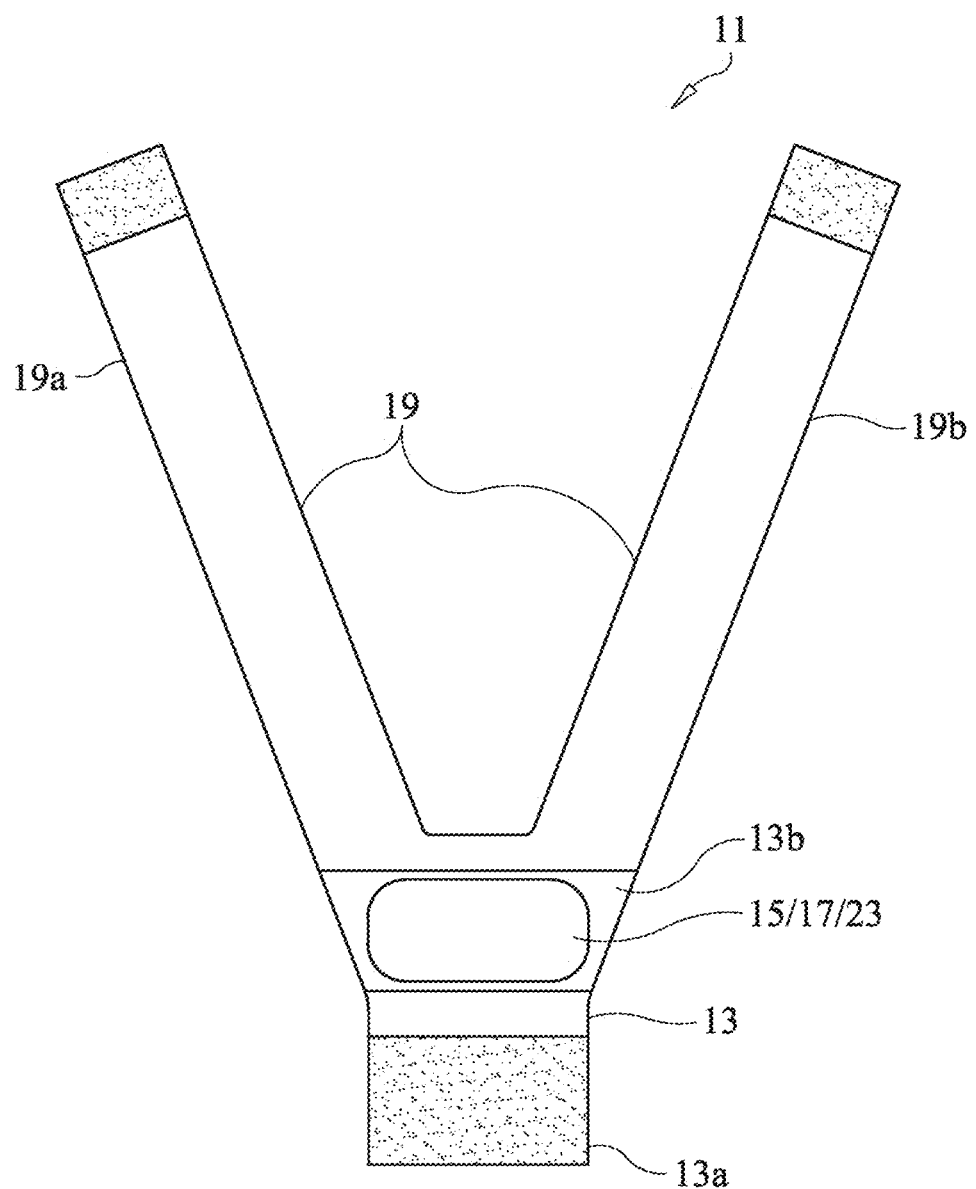
FIG. 2 is a plan view of the ulnar impingement device according to an embodiment of the present invention.
Figure 3:
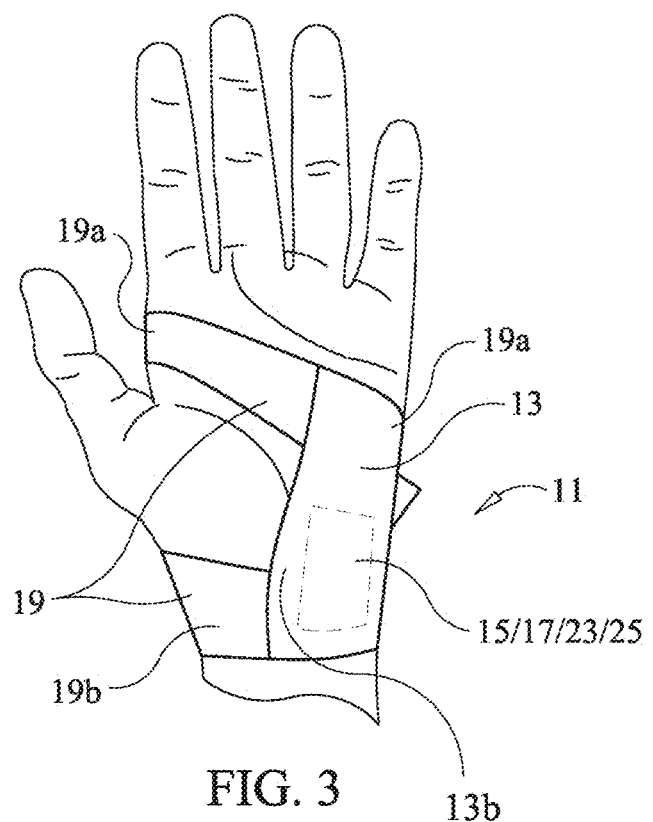
FIG. 3 is a view showing the ulnar impingement device applied to a patient according to an embodiment of the present invention.
Figure 4:
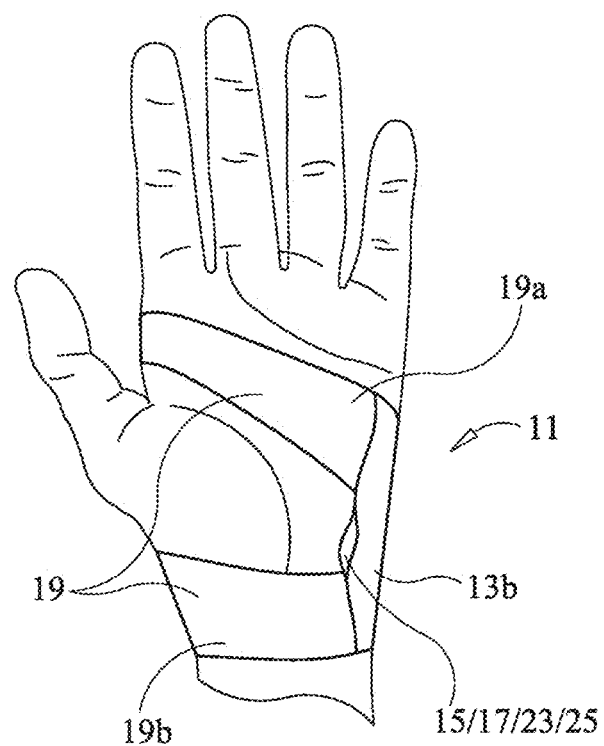
FIG. 4 is another view showing the bladder or impinger of the ulnar impingement device applied to a patient according to an embodiment of the present invention.
Figure 5:
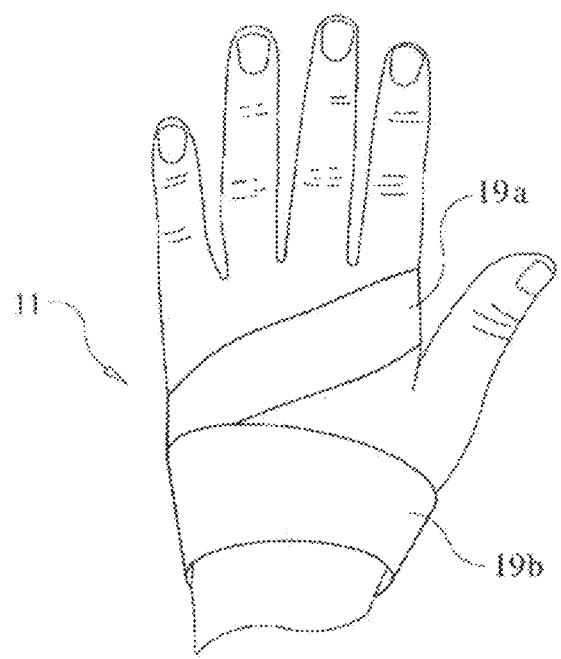
FIG. 5 is a view showing the ulnar impingement device applied to a patient showing the top of the hand according to an embodiment of the present invention.
Figure 6:
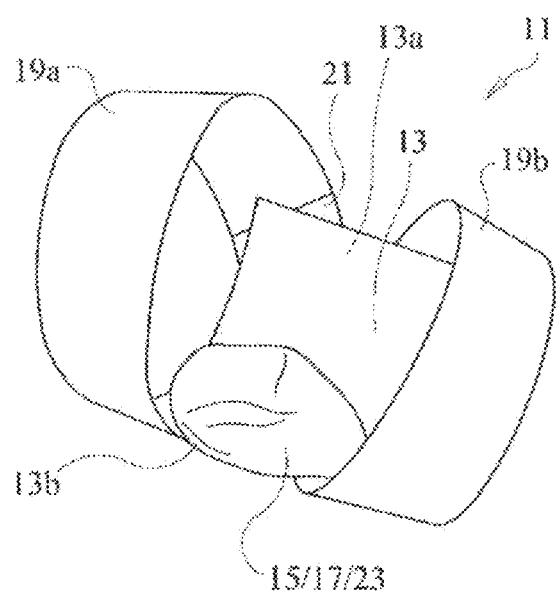
FIG. 6 is an isometric view of the ulnar impingement device shown with trunk fastened to the pair of limbs.

A present invention method of catheterization of the radial artery directed at minimizing occurrences of radial artery occlusion is disclosed. Referring to FIG. 1 specifically, and the Figures in general, the method 1000 comprises inserting a sheath into the radial artery of a patient at an access site. A sheath, as disclosed herein, is understood to encompass any device inserted into the radial artery and used to permit the access of instrumentation into the radial artery. The desired catheterization procedure is then performed using the sheath to provide instrumentation access the radial artery.

Once the catheterization procedure is complete, an ulnar pressure is applied to the homolateral ulnar artery at an ulnar pressure site while the sheath remains inserted in the radial artery. The sheath is then removed from the radial artery while maintaining the first pressure to the ulnar artery. Once the sheath is removed, and while continuing to apply the ulnar pressure, pressure is applied to the radial artery at the access site to obtain hemostasis at the access site.

In a preferred embodiment, the step of "applying a pressure to the radial artery at the access site to obtain hemostasis at the access site" is accomplished while maintaining the first pressure to the ulnar artery.

The radial artery and the ulnar artery are the two conduits for the flow of oxygenated blood to the hand. The arteries are interconnected and therefore form an interdependent flow network. When flow is reduced in one of the arteries, by compression for example, flow increases in the other artery. When the ulnar artery is compressed, flow in the ulnar artery is reduced, which causes an increase in pressure and flow in the radial artery. When the radial artery is compressed, flow in the radial artery is reduced, which causes an increase in pressure and flow in the ulnar artery.

In an embodiment, a further step includes confirming that the application of ulnar pressure has reduced blood flow through the ulnar artery. This is done by monitoring flow of the ulnar artery prior to and after applying the ulnar pressure. In a further embodiment, monitoring flow of the ulnar artery includes sensing skin blood flow and/or pulsation at a fingertip or other location downstream of the ulnar pressure site. Digital plethysmography is employed in one embodiment.

In another embodiment, the method 1000 further includes confirming patency of the radial artery during the step of applying a pressure to the radial artery. In a preferred embodiment, patency is accomplished by sensing skin blood flow and/or pulsation at a fingertip or other location downstream of the access site. Other sensing locations both upstream and downstream may be used to confirm patency of the radial artery. In the preferred embodiment, the sensing is performed while the ulnar artery is fully compressed (allowing no flow through the ulnar artery) and/or partially compressed (allowing less flow than when not compressed at all). Patency is confirmed, in an embodiment, by obtaining a metric relating to the sensing and comparing the metric with a standard metric for the patient, or with a previously-sensed metric. Metric is understood to mean a sensible, quantifiable value or reading, relating to the characteristic sensed. Preferably, the previously sensed metric is read after the applying the ulnar pressure step and before the step of removing the sheath from the radial artery. Digital plethysmography is employed, in a preferred embodiment, to obtain the metrics. Other sensing modes may be employed, so long as the selected mode is capable of confirming patency in one form or another.

In an embodiment of the present invention method 1000, the step of compressing the ulnar artery includes: providing an ulnar impinger, securing the ulnar impinger over the wrist such that the impinger contacts a first location over the ulnar artery, and activating the impinger to press on the ulnar artery at the first location. In a preferred embodiment, the first location is over the Guyon's canal, demarcated by pisiform bone on the medial aspect, directly over the ulnar artery pulse.

Impinger is understood to include any device capable of applying a force to the ulnar artery, whether alone or part of a system, sufficient to compress the ulnar artery. One exemplary class includes mechanical devices that expand in size to cause a band surrounding the wrist to constrict an object to compress the ulnar artery. Another exemplary class of impingers includes mechanical devices that constrict a band worn around the wrist sufficient to cause an object to press on the ulnar artery.

In a preferred embodiment, the step of compressing the ulnar artery includes: providing an ulnar impingement band having an inflatable bladder, securing the ulnar impingement band over the wrist such that the bladder contacts a first location over the ulnar artery, and inflating the bladder to impinge upon the ulnar artery at the first location.

Turning to the Figures generally, and particularly FIGS. 2-6, there is further disclosed a device 11 for use in applying a compressing force to the ulnar artery of a patient. The device 11 includes a trunk 13 having an inflatable bladder 15. The trunk 13 is defined by a lower portion 13a and an upper portion 13b. The bladder 15 is defined by an envelopment 17 existing between the lower portion 13a and the upper portion 13b. A pair of limbs 19 are connected to and extend from the upper portion 13b of the trunk 13. Together, the pair of limbs 19 and the trunk 13 form a general Y-shape. Preferably, the pair of limbs 19 and the trunk 13 are planar and form a Y-shape band. A first limb 19a of the pair of limbs 19 is adapted to lay across the palm of a hand, between the thumb and the index finger. The first limb 19a is adapted to connect to the trunk 13 for securing the first limb 19a to the trunk 13 and for securing the bladder 15 to a portion of the patient's wrist corresponding with a first location 25 over the ulnar artery. A second limb 19b of the pair of limbs 19 is adapted to lay over the wrist/distal forearm and connect to the trunk 13. This is to secure the second limb 19b to the trunk 13 and to further secure the bladder 15 to the first location 25 over the ulnar artery. One or more connectors 21 are utilized for fixing the pair of limbs 19 to the trunk 13. In a preferred embodiment, the connector is Velcro.

In use, the bladder 15 is located at the first location 25 over the ulnar artery, and the pair of limbs 19 are fixed around the hand and wrist to the trunk 13 with the connectors 21. The bladder 15 is inflated with a tube connected to an inflator to cause the bladder 15 to impinge upon the ulnar artery at the first location 25.

There is further disclosed a device 13 for use in applying a compressing force to the ulnar artery of a patient. The device 13 comprises a trunk 13 having an impinger 23. The trunk 13 is defined by a lower portion 13a and an upper portion 13b. The impinger 23 is defined by any device sufficient to apply a compression force. Examples include expanding springs, expanding screw-type appurtenances, or other devices and systems as discussed herein. A pair of limbs 19 are connected to and extend from the upper portion 13b of the trunk 13. The pair of limbs 19 together with the trunk 13 form a general Y-shape. A first limb 19a of the pair of limbs 19 is adapted to lay across the palm of a hand, between the thumb and the index finger. The first limb 19a connects to the trunk 13 to secure the first limb 19a to the trunk 13, and also to secure the impinger 23 to a portion of the patient's wrist corresponding with a first location 25 over the ulnar artery. A second limb 19b of the pair of limbs 19 is adapted to lay over the wrist/distal forearm and connect to the trunk 13 to secure the second limb 19b to the trunk 13 and to further secure the impinge 23 to the first location over the ulnar artery. One or more connectors 21 are employed to fix the pair of limbs 19 to the trunk 13. In use, the impinger 23 is located at the first location 25 over the ulnar artery. The pair of limbs 19 are fixed around the hand and wrist to the trunk 13 with the connectors 21. The impinger 23 is activated to cause the impinger 23 to impinge upon the ulnar artery at the first location 25.

In another embodiment of the present invention method 1000, an introducer sheath and/or a catheter is placed in a radial artery after sterile preparation as well as with administration of local anesthetic. The radial artery is punctured at an access site and, after placement of a guidewire, either an introducer sheath or a catheter is introduced in the radial artery lumen. The catheterization procedure is performed in a manner deemed appropriate by the operator.

In one embodiment, the present invention method further comprises administering an anticoagulant at any time after introduction of the catheter or introducer sheath and before removal of the catheter or the introducer sheath. In another embodiment, an anticoagulant is administered before the introduction of the catheter or introducer sheath. Examples of anticoagulants include, without limitation, unfractionated heparin, bivalirudin or Enoxaparin. In one embodiment, wherein a method for obtaining patent hemostasis at an access site of an artery comprises increasing the flow of blood in the artery that is punctured at the access site, unfractionated heparin is administered at a dose that is lower than a conventional dose.

The flow of blood is increased in the radial artery if the radial artery is punctured for catheterization; the flow of blood is increased in the ulnar artery if the ulnar artery is punctured for catheterization; the flow of blood is increased in femoral artery if the femoral artery is punctured for catheterization; or the flow of blood is increased in any other artery that is punctured at an access site. The flow of blood in an artery can be increased by different techniques. For example, the flow of blood in artery can be increased by a pharmacological method, e.g., administration of a drug. Examples of drugs that can be used to increase the flow of blood in an artery include vasodilators that reduce distal resistance and increase proximal flow, which include all vasodilator agents (e.g., nitrates, calcium channel blockers) or agents that increase cardiac output (e.g., dobutamine, epinephrine, milrinone). The flow of blood in an artery can also be increased using external forces. For example, flow of blood in a radial artery can be increased by applying a compressive force on the ulnar artery, and the flow of blood in the ulnar artery can be increased by applying a compressive force on the radial artery. The flow of blood in an artery could also be increased by using mechanical devices, e.g., pump. The device could be implantable in the human body or external to the human body. For example, use of a pump to increase flow of blood in a femoral artery is known in the art.

Increasing the flow of blood in an artery leads to an increase in the velocity of blood in the artery. The increase in velocity results in decrease in residence time or contact time of blood at the puncture site on the artery. The residence time or contact time (t, seconds) is calculated by dividing the diameter (d, mm) of the puncture hole with the velocity (v, mm/second) of the blood in the artery. $t=d/v$. For a given puncture hole with diameter (d), higher the velocity (v), lower is the contact time t. A lower contact time results in lower exposure of blood to external environment thereby lowering the potential for transmural clotting and vessel lumen occlusion during the catheterization procedure. A lower than conventional dose of anticoagulant can then be used by increasing the flow of blood in an artery punctured for a catherization procedure.

In one embodiment, a method of reducing dosage of an anticoagulant when performing a catheterization procedure at an access site of an artery comprises administering the anticoagulant at a dosage less than a conventional dose of an equivalent of 50 units of unfractionated heparin per kg of body weight, obtaining an increase in velocity of blood in the artery that is punctured at the access site, and maintaining the increase in the velocity of blood in the artery for a period of time during the catheterization procedure. In another embodiment, a method of reducing a dosage of an anticoagulant when performing a catheterization procedure at an access site of an artery comprises administering the anticoagulant at a dose less than a conventional dose of an equivalent of 50 units of unfractionated heparin per kg of body weight, reducing a contact time of blood at the access site of the artery, and maintaining the contact time of blood at a reduced level for a period of time during the catheterization procedure. Unfractionated heparin or another anticoagulant may be used at a dose that is lower than a conventional dose. An anticoagulant is selected from a group comprising heparin, dalteparin, Fragmin®, danaparoid, enoxaparin, unfractionated heparin, other low molecular weight heparin, direct thrombin inhibitors including hirudin, argatroban, bivalirudin and all substances derived from and/or related to the foregoing substances.

In one embodiment, the anticoagulant is unfractionated heparin and the dosage of the unfractionated heparin is less than 50 units per kilogram of body weight, administered parenterally. In yet another embodiment, the dosage of unfractionated heparin is about 25 units per kilogram of body weight. In another embodiment, the dosage of unfractionated heparin is less than 25 units per kilogram of body weight. In yet another embodiment, the dosage of unfractionated heparin is in the range of 20-40 units per kilogram of body weight. In another embodiment, the dosage of unfractionated heparin is in the range of 15-30 units per kilogram of body weight. The dosage of other anticoagulants is similar to dosage of unfractionated heparin and is measured as equivalent of units of unfractionated heparin per kg of body weight.

After completion of the catheterization procedure, the present invention method comprises applying hemostatic compression to the access site using a device. In one embodiment, the device is a band having at least two inflatable bladders wherein one inflatable bladder is used to apply compressive hemostatic pressure at the access site on the radial artery, and a second inflatable bladder is used to apply an ulnar pressure at an ulnar pressure site. In another embodiment, a device such as an impinger that is capable of applying a mechanical compressive force is used to apply the ulnar pressure. In yet another embodiment, a device such as an impinger that is capable of applying a mechanical compressive force is used to apply the compressive hemostatic pressure at the access site on the radial artery. In another embodiment, a band with at least one inflatable bladder is used to apply compressive hemostatic pressure at the access site on the radial artery, and another device is used to apply ulnar pressure at an ulnar pressure site. Manual compression may also be used.

The band having at least two inflatable bladders is wrapped around the wrist of a patient, and secured near both ends of the band with fastener. In one embodiment, the first bladder covering the puncture site on the radial artery is filled with air to apply a first occlusive pressure to the radial artery, thereby stopping both bleeding and intra-arterial blood flow at the puncture site. Then, the second balloon covering the ulnar artery is filled with air to apply a second occlusive pressure to the ulnar artery, thereby stopping intra-arterial blood flow. As a result, there will be limited blood supply to the hand as occlusive pressure on both the radial artery and the ulnar artery has been applied. Subsequently, pressure on the radial artery is released over a period of time by slowly deflating the first bladder until a blood spurt is seen from the puncture site of the radial artery under the first bladder. Once blood flow from the puncture site has been observed, the pressure in the first bladder covering the puncture site is slightly increased by introducing small amount of air to stop the bleeding. In one embodiment, inflation of the balloons is done manually using syringes to inject fluid, e.g., air in the balloons. In another embodiment, deflation of the balloons is also done manually using syringes to remove fluid from the balloons. In yet another embodiment, deflation of balloons is done automatically using valves designed to eject fluid from a balloon periodically over a period of time.

In one embodiment of the present invention method, wherein an anticoagulant such as unfractionated heparin is administered to a patient, the method further comprises applying hemostatic compression for a time less than 120 minutes. In another embodiment, the hemostatic compression time is about 60 minutes. In yet another embodiment, the hemostatic compression time is less than 60 minutes. In one embodiment, during the hemostatic compression time when the radial artery is compressed at the access site, the ipsilateral ulnar artery is also compressed simultaneously. In another embodiment, the ipsilateral ulnar artery is compressed continuously during the entire hemostatic compression time. In yet another embodiment, the ipsilateral ulnar artery is compressed continuously for only a part of the hemostatic compression time. In another embodiment, the ulnar artery is compressed intermittently during the hemostatic compression time. In some embodiments, the ulnar artery may be compressed fully, and in other embodiments, the ulnar artery may be compressed partially.

In one embodiment of present invention, a method of obtaining hemostasis of a radial artery of a patient after performing a catheterization procedure at an access site of the radial artery, comprises performing the following steps: (a) applying a hemostatic pressure to the radial artery at the access site; (b) providing an increased flow of blood in the radial artery; (c) administering a dose of unfractionated heparin to the patient; and (d) maintaining simultaneously the hemostatic pressure and the increased flow of blood in the radial artery; wherein step (b) comprises applying an ulnar pressure to an ulnar artery at an ulnar pressure site; and wherein step (c) comprises administering the dose of unfractionated heparin that is less than 50 units per kg body weight.

In another embodiment of present invention, a method of obtaining hemostasis of an artery of a patient after performing a catheterization procedure at an access site of the artery, comprises performing the following steps: (i) applying a hemostatic pressure to the artery at the access site; (ii) providing an increased flow of blood in the artery; (iii) administering a dose of unfractionated heparin or other anticoagulant to the patient; and (iv) maintaining simultaneously the hemostatic pressure and the increased flow of blood in the artery for a duration of time; wherein step (iii) comprises administering the dose of unfractionated heparin that is less than 50 units per kg body weight; and wherein the duration of time in step (iv) is less than 120 minutes.

In yet another embodiment of the present invention, a method of obtaining hemostasis of a radial artery of a patient after performing a catheterization procedure at an access site of the radial artery, comprising performing the following steps: (A) applying a hemostatic pressure to the radial artery at the access site; (B) providing an increased flow of blood in the radial artery; (C) administering a dose of an anticoagulant to the patient; and (D) maintaining simultaneously the hemostatic pressure and the increased flow of blood in the radial artery for a duration of time; wherein step (B) comprises applying an ulnar pressure to an ulnar artery at an ulnar pressure site; wherein the dose of the anticoagulant in step (C) is less than an equivalent of 50 units of unfractionated heparin per kg of body weight; and wherein the duration of time in step (D) is less than 120 minutes. In one embodiment, the increased flow of blood in the radial artery is provided by compressing the ulnar artery.

In one embodiment of the present invention, a hemostatic pressure on the radial artery is applied using a first band comprising at least one inflatable bladder, wherein the inflatable bladder of the first band applies the hemostatic pressure at the access site, and the ulnar pressure is applied using a technique selected from a group consisting of (i) a second band comprising at least one inflatable bladder, wherein the inflatable bladder of the second band applies a pressure at the ulnar pressure site, (ii) a mechanical device applies a compressing force at the ulnar pressure site; (iii) manual pressure is applied at the ulnar pressure site.

In one embodiment, after about 60 minutes of compression of the radial artery at the access site, the pressure of compression is gradually reduced and weaned off from the radial artery access site, and the site is lightly dressed. In another embodiment, the duration of reducing the compression and weaning off the hemostatic compression pressure is in the range of 5-10 minutes. This technique improves patient comfort and increases the number of patients who can be treated.

In another embodiment, a method of obtaining hemostasis of a radial artery of a patient when performing a catheterization procedure at an access site of the radial artery, comprises administering a dose of an anticoagulant to the patient during the catheterization procedure and performing the following steps: (a) applying a hemostatic pressure to the radial artery at the access site for a duration of time at least until hemostasis of the radial artery; (b) applying an ulnar pressure to an ulnar artery at an ulnar pressure site to fully compress the ulnar artery, thereby providing an increased flow of blood in the radial artery; (c) applying an ulnar pressure to the ulnar artery at the ulnar pressure site to partially compress the ulnar artery, thereby providing an increased flow of blood in the radial artery; (d) maintaining simultaneously the hemostatic pressure and the increased flow of blood in the radial artery; and attaining hemostasis of the radial artery. In one embodiment, step (b) precedes step (c). In another embodiment, step (c) comprises continuous partial compression of the ulnar artery at least until hemostasis of the radial artery.

In yet another embodiment, a method of obtaining hemostasis of a radial artery of a patient when performing a catheterization procedure at an access site of the radial artery, comprises performing the following steps: (a) administering a dose of an anticoagulant to the patient during the catheterization procedure, (b) applying a hemostatic pressure to the radial artery at the access site for a duration of time at least until hemostasis of the radial artery; (c) applying an ulnar pressure to an ulnar artery at an ulnar pressure site to fully compress the ulnar artery; (d) applying continuously an ulnar pressure to the ulnar artery at the ulnar pressure site to partially compress the ulnar artery for a part of the duration of time; and attaining hemostasis of the radial artery; wherein step (a) precedes all other steps, and step (c) precedes step (d).

In another embodiment, a method of obtaining hemostasis of a radial artery of a patient when performing a catheterization procedure at an access site of the radial artery, comprises performing the following steps: (a) administering a dose of an anticoagulant to the patient during the catheterization procedure; (b) applying a hemostatic pressure to the radial artery at the access site for a duration of time at least until hemostasis of the radial artery; (c) applying an ulnar pressure to an ulnar artery at an ulnar pressure site to fully compress the ulnar artery; (d) applying an ulnar pressure to the ulnar artery at the ulnar pressure site, wherein the ulnar pressure is applied intermittently; and (e) attaining hemostasis of the radial artery; wherein step (a) precedes all other steps, and step (c) precedes step (d). In yet another embodiment, the ulnar pressure in step (d) is applied intermittently at least until hemostasis of the radial artery.

Figure 7:
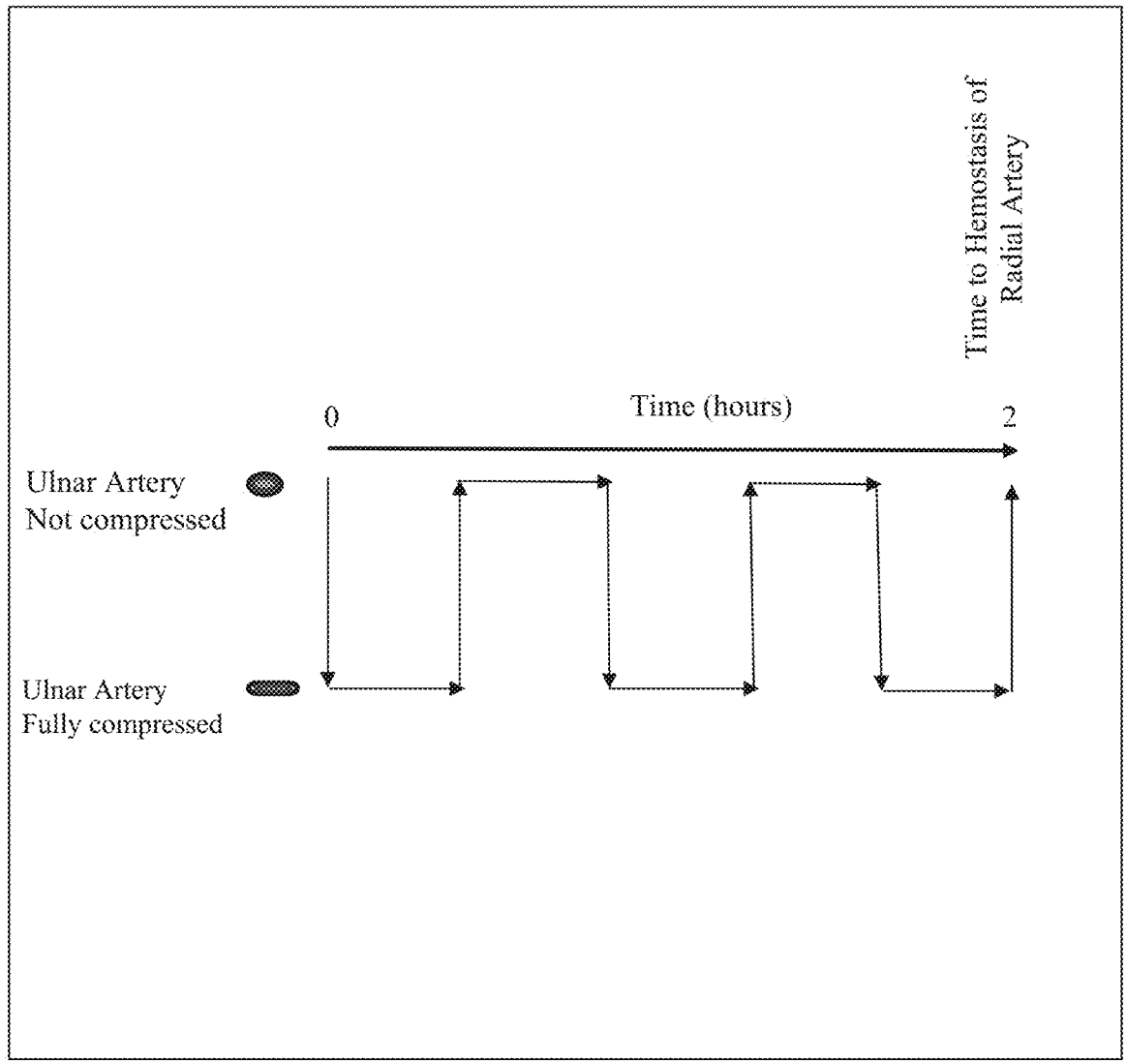
FIG. 7 is a schematic depiction of an embodiment of the invention wherein the ulnar artery is compressed to a point of occlusion intermittently over the duration of time to obtain hemostasis of the radial artery.

A period of 2 hours (120 minutes) is the time it typically takes for hemostasis to occur. In practice, the time for hemostasis could last for more than 2 hours or less than 2 hours. An important consideration during the hemostasis process is hand ischemia. The risk of hand ischemia has to be minimized and the benefit of patent hemostasis maximized. Because the radial artery is generally compressed continuously at the radial puncture site for about 2 hours to obtain hemostasis, one safe approach considering the potential for hand ischemia is to compress the ulnar artery to a point of occlusion intermittently over the duration of time for hemostasis, i.e., compressing the ulnar artery fully for several minutes and then removing the pressure on the ulnar artery for several minutes and repeating the cycle, thereby providing periodic blood flow to the hand during the hemostasis period. FIG. 7 is a schematic depiction of an embodiment of the invention wherein the ulnar artery is compressed to a point of occlusion intermittently over the duration of time to obtain hemostasis of the radial artery. Note that the X-axis in FIG. 7 (and FIGS. 8-15) is the time taken to obtain hemostasis of the radial artery. FIGS. 7-15 show the time as 2 hours, however it should be noted that the time to obtain hemostasis can be more than 2 hours or less than 2 hours. So, for example, if the time to obtain hemostasis is 1 hour, then the number 2 on the X-axis should be replaced with number 1. The Y-axis depicts the compression of the ulnar artery, i.e., whether the ulnar artery is fully compressed, partially compressed or not compressed.

Figure 8:
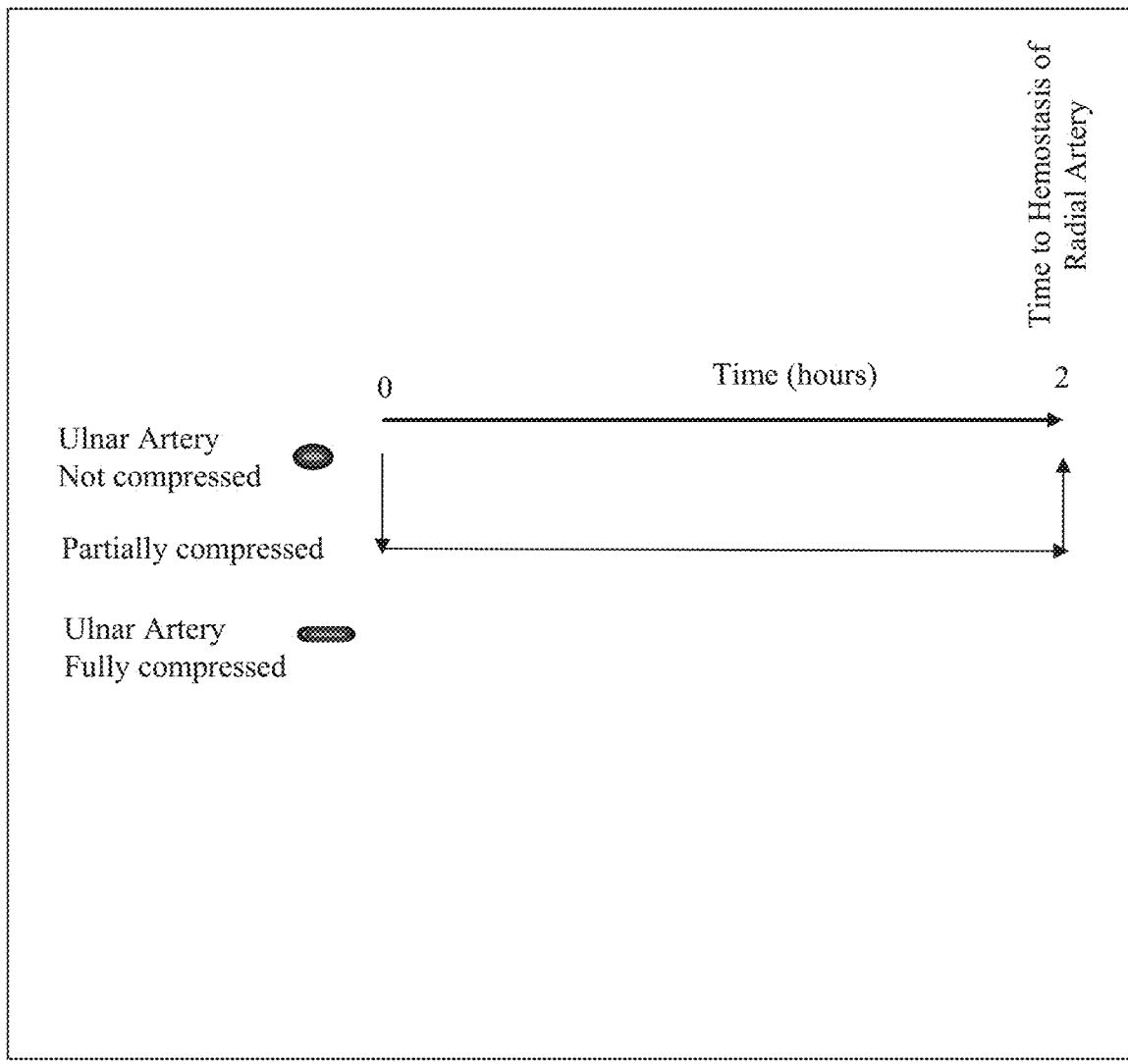
FIG. 8 is a schematic depiction of an embodiment of the invention wherein the ulnar artery is compressed partially over the duration of time to obtain hemostasis of the radial artery.
Figure 9:
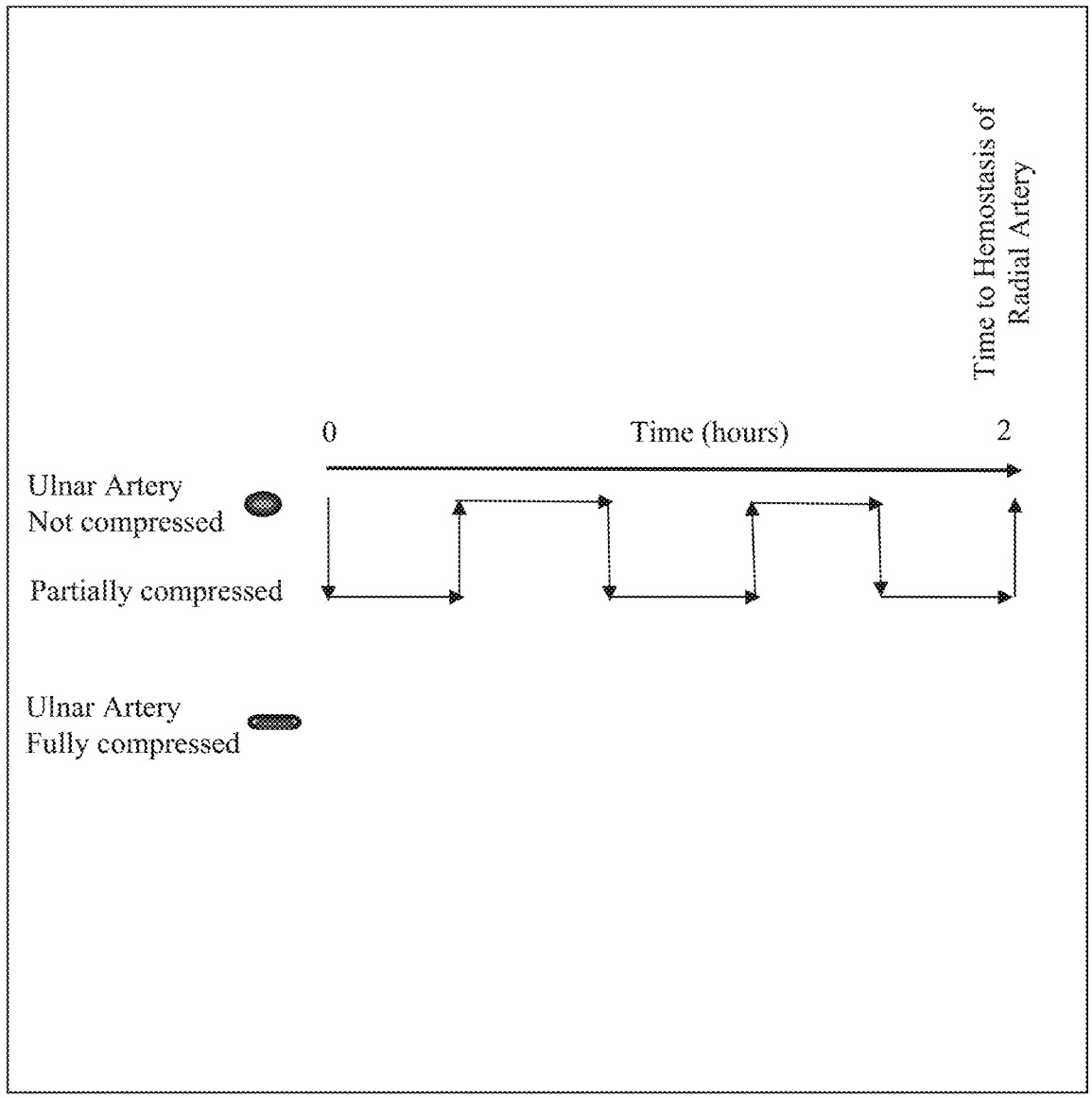
FIG. 9 is a schematic depiction of an embodiment of the invention wherein the ulnar artery is compressed partially and intermittently over the duration of time to obtain hemostasis of the radial artery.
Figure 10:
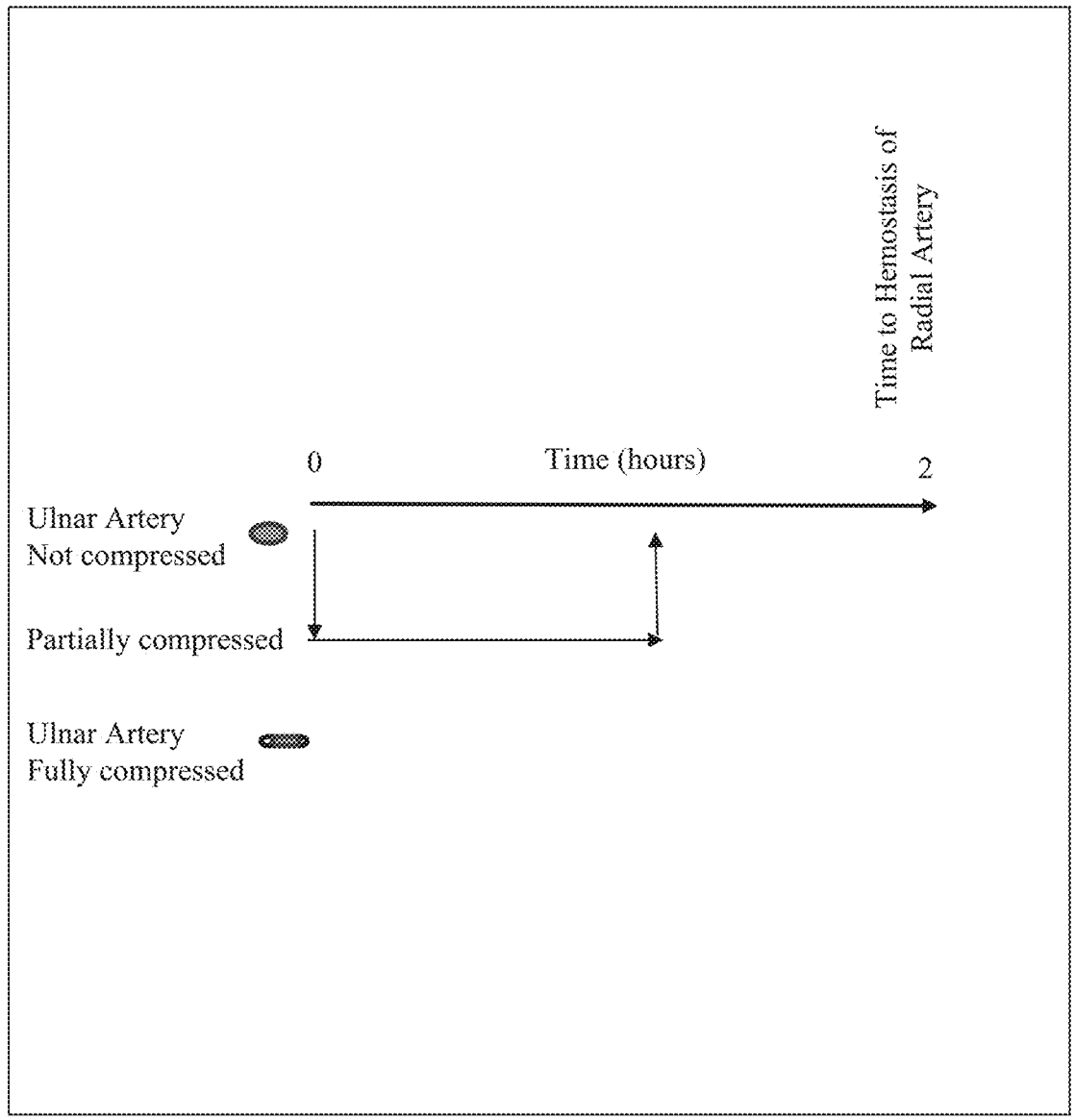
FIG. 10 is a schematic depiction of an embodiment of the invention wherein partial compression of the ulnar artery is maintained for a part of the duration of time required to obtain hemostasis of the radial artery.
Figure 11:
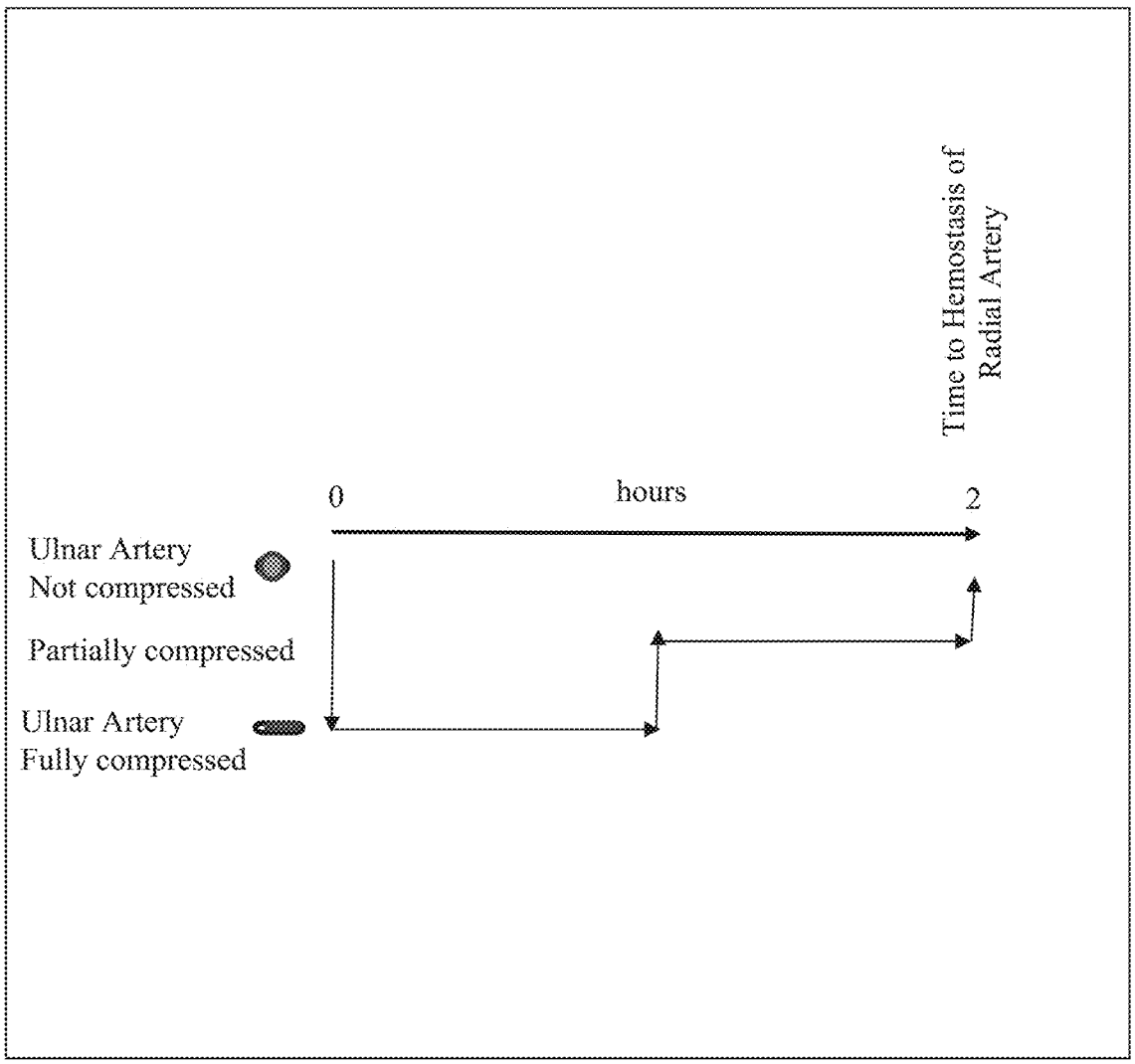
FIG. 11 is a schematic depiction of an embodiment of the invention wherein the ulnar artery is fully compressed for a fraction of the duration of time required to obtain hemostasis of the radial artery and partially compressed for the remainder of the period.
Figure 12:
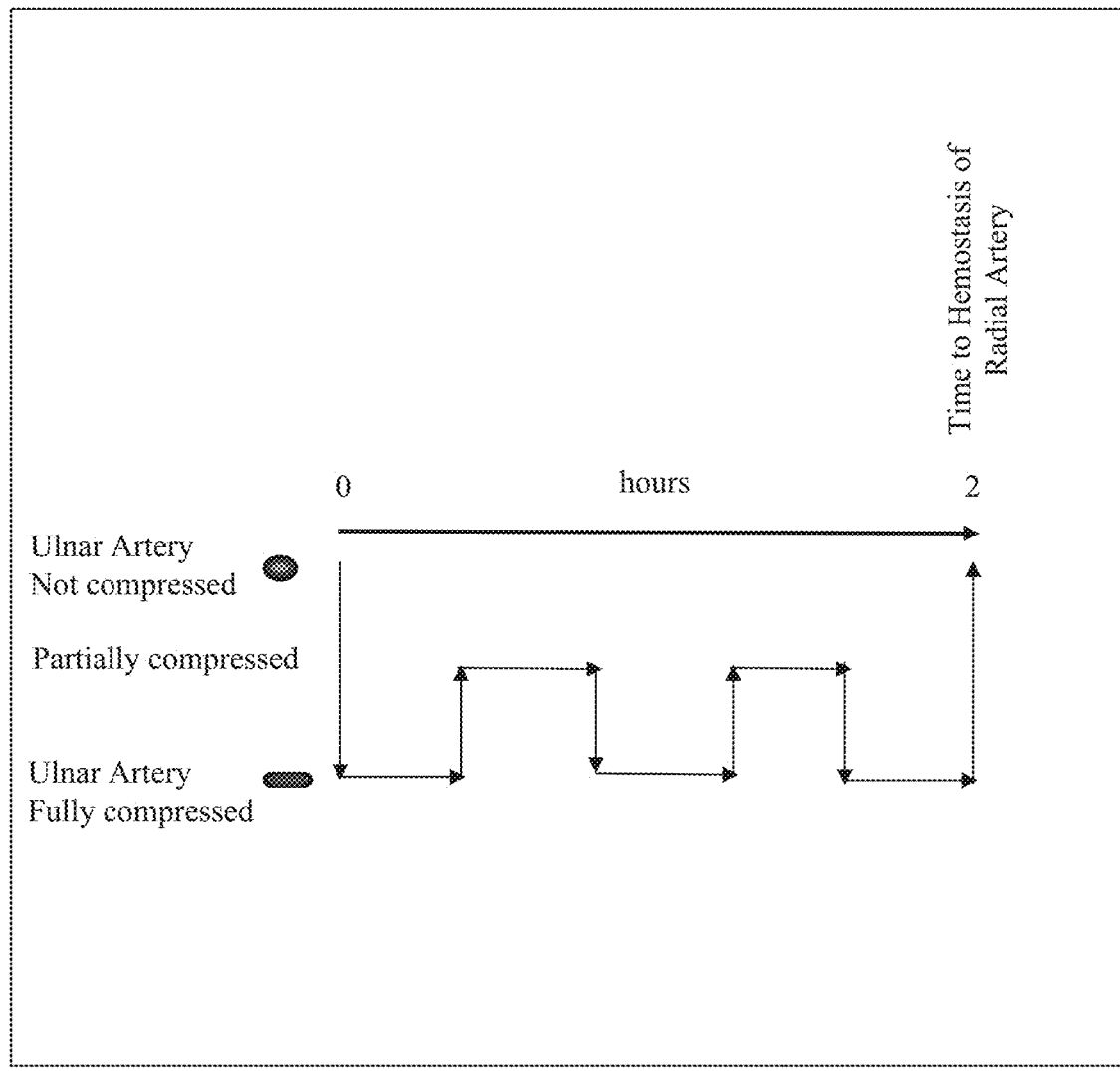
FIG. 12 is a schematic depiction of an embodiment of the invention wherein the ulnar artery is fully compressed for a fraction of the duration of time required to obtain hemostasis of the radial artery and partially compressed for the remainder of the period.

In another embodiment of the invention as shown schematically in FIG. 8, patent hemostasis is obtained by compressing the ulnar artery partially and maintaining continued partial compression of the ulnar artery while simultaneously compressing the radial artery over the duration of time to obtain hemostasis of the radial artery. Partial compression of the ulnar artery would provide some blood flow to the hand. In yet another embodiment, the ulnar artery is compressed partially and intermittently as shown in FIG. 9. In another embodiment shown schematically in FIG. 10, partial compression of the ulnar artery is maintained for a part of the duration of time required to obtain hemostasis of the radial artery. In another embodiment, the ulnar artery is compressed partially for a first period of time, and the pressure is increased to compress the ulnar artery fully for a second period of time.

Figure 13:
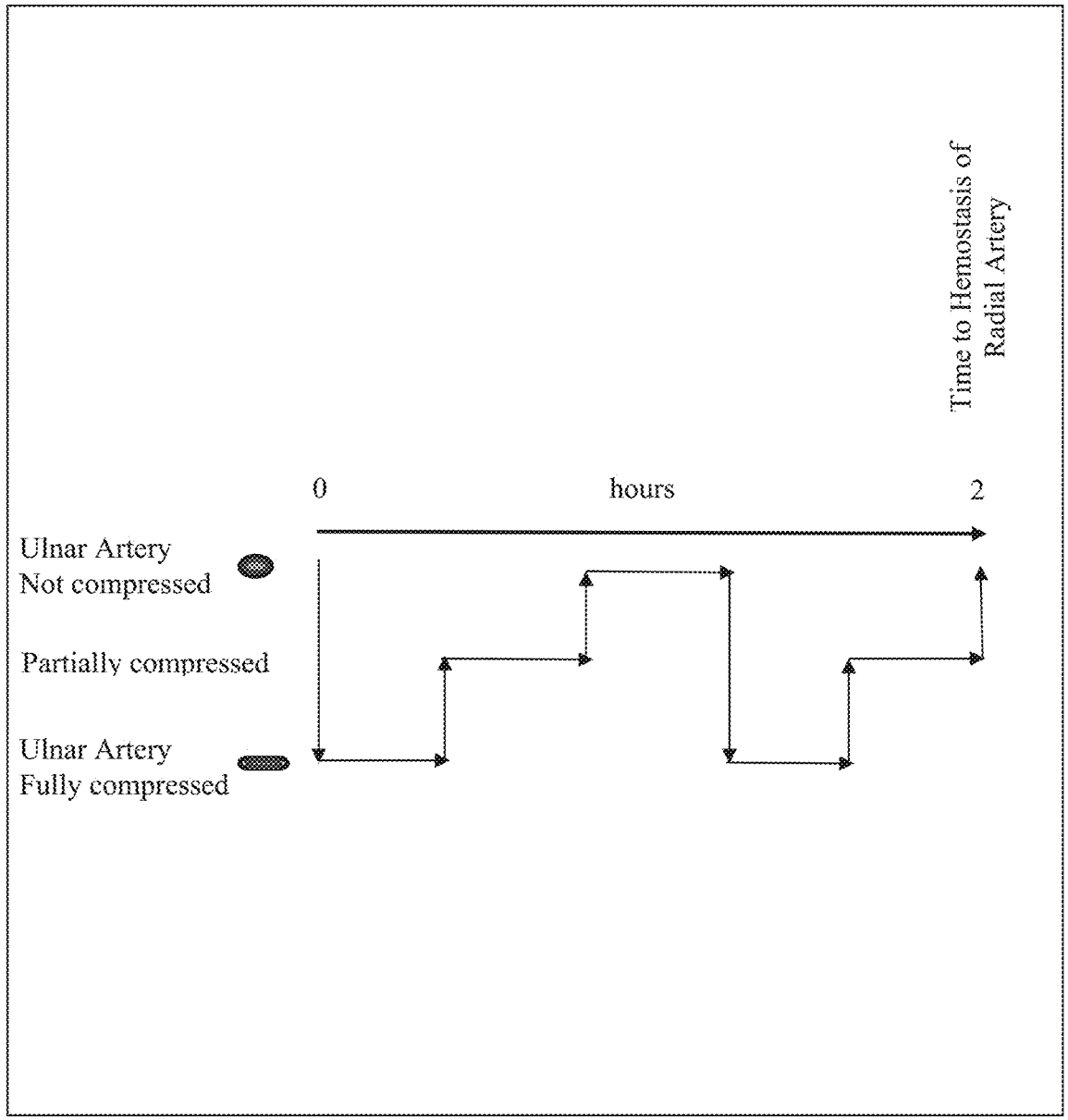
FIG. 13 is a schematic depiction of an embodiment of the invention wherein the ulnar artery is fully compressed for a fraction of the time required to obtain hemostasis of the radial artery, the compressive force is then released in a stepwise manner. The compression and the release is then repeated.
Figure 14:
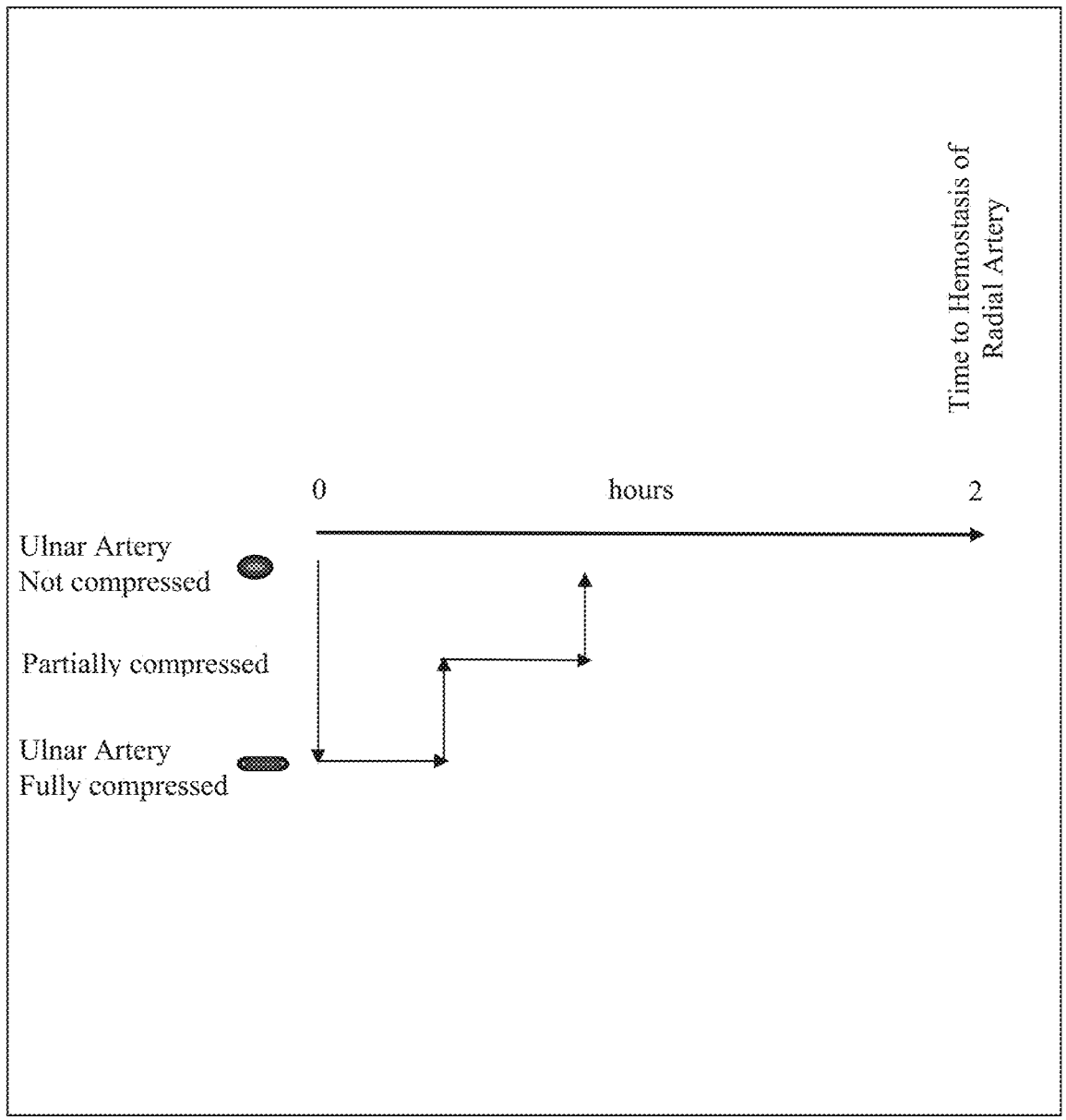
FIG. 14 is a schematic depiction of an embodiment of the invention wherein the ulnar artery is fully compressed for a fraction of the time required to obtain hemostasis of the radial artery, the compressive force is then released in a stepwise manner.
Figure 15:
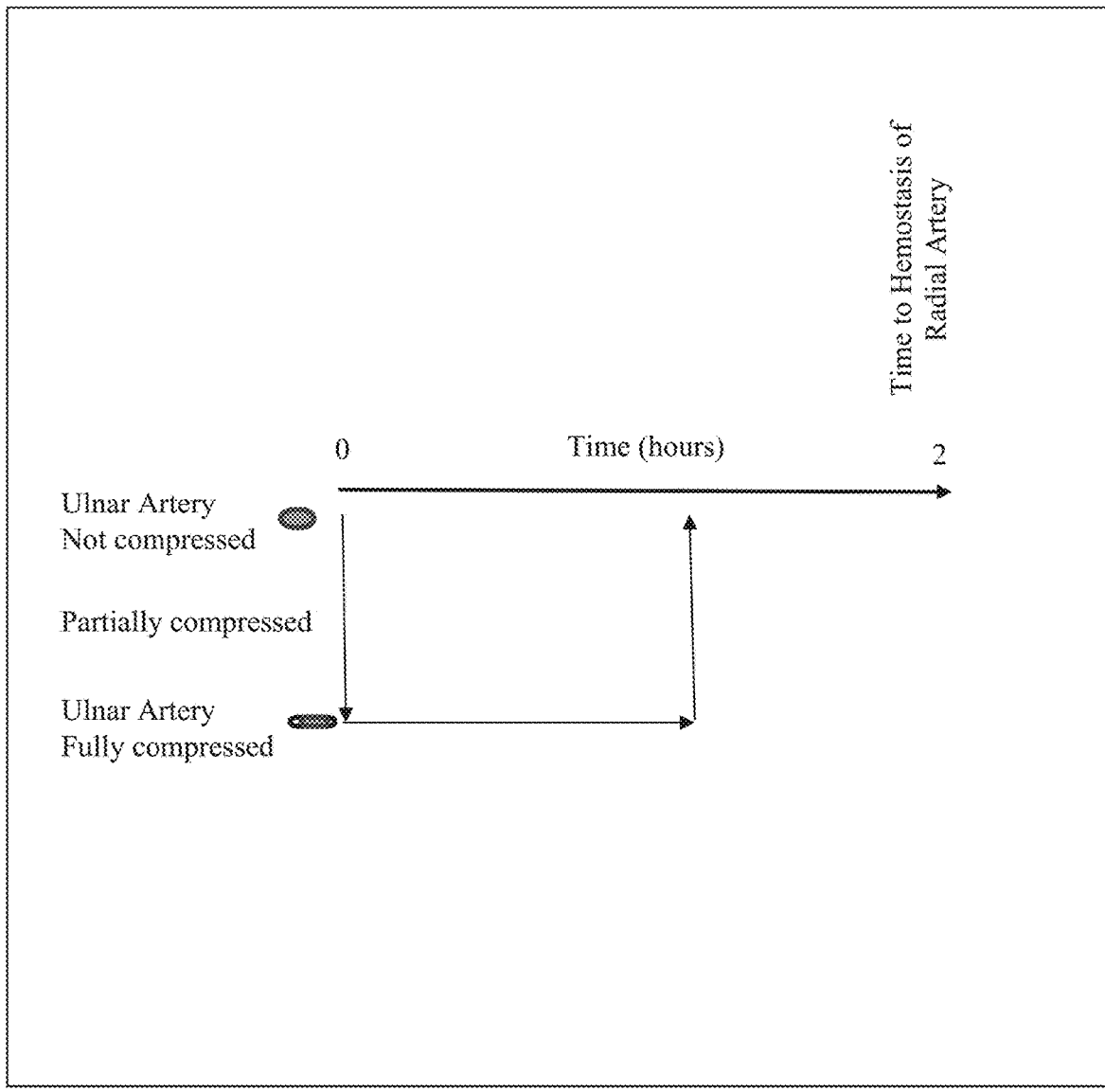
FIG. 15 is a schematic depiction of an embodiment of the invention wherein the ulnar artery is fully compressed for a part of duration of time required to obtain hemostasis of the radial artery.

In one embodiment, ulnar artery is compressed continuously for the duration of time at least until hemostasis of the radial artery wherein the ulnar artery is fully compressed for a fraction of the duration of time and partially compressed for the remainder of the period. See, for example, FIGS. 11 and 12. And there are embodiments as shown in FIGS. 13 and 14 wherein the ulnar artery is fully compressed for a fraction of the time required to obtain hemostasis of the radial artery, the compressive force is then released in a stepwise manner. In yet another embodiment, the compressive force is released in a linear manner or a continuous curvilinear manner rather than a stepwise manner over a period of time. In another embodiment of the method invention depicted in FIG. 15, the ulnar artery is fully compressed for a part of duration of time required to obtain hemostasis of the radial artery.

In an embodiment of the invention, a band comprising a radial balloon and an ulnar balloon is applied to the instrumented forearm with the radial balloon above or at the radial puncture site, and the distal end of the band aligned with the crease of the wrist at the distal end of the forearm. The ulnar balloon is inflated to totally occlude the ulnar artery flow at the outset. Then inflate the radial balloon, and remove the introducer sheath, observe the puncture site and inflate the radial balloon to the point where there is no further bleeding from the radial puncture site. In about 15 minutes after full compression of the ulnar artery, and no later than 30 minutes, deflate the ulnar balloon to allow flow in the ulnar artery, making the ulnar artery partially compressed. In another embodiment, reduce the pressure on the ulnar artery to zero in the time range of about 15 minutes to about 30 minutes after full compression of the ulnar artery. Adjust the pressure in the radial balloon to allow for radial artery patency and for maintenance of radial hemostasis. Deflate the ulnar balloon partially or fully at any point if the patient experiences discomfort at the ulnar compression site.

Figure 16:
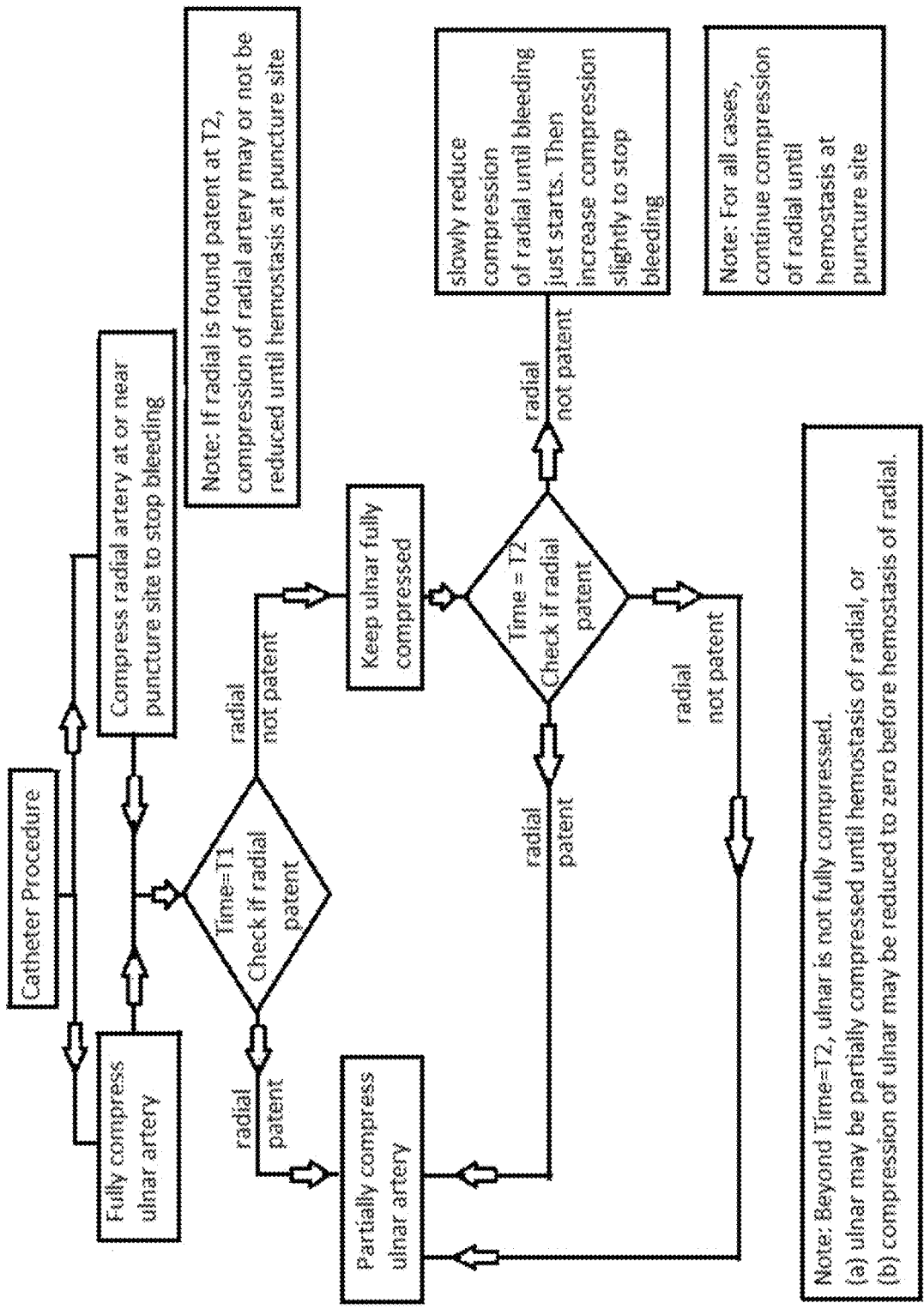
FIG. 16 is a schematic diagram of an embodiment of the invention depicting the steps to obtain patent hemostasis of the radial artery by compressing the ulnar artery.

In another embodiment as shown in FIG. 16, after completing the catheterization procedure, pressure is applied to ulnar artery to fully compress the ulnar artery and pressure is applied to the puncture site of the radial artery to stop bleeding. In one embodiment, pressure is applied to the ulnar artery before the pressure is applied to the radial artery. In another embodiment, pressure is applied to the radial artery before the pressure is applied to the ulnar artery. Measure time from the time ulnar artery was fully compressed. At time=T1 from the time ulnar artery was fully compressed, check whether the radial artery is patent. If the radial artery is patent, deflate the ulnar balloon to partially compress the ulnar artery. If the radial artery is not patent at time=T1, continue full compression of the ulnar artery until time=T2. Check again the patency of radial artery at time=T2. If the radial artery is not found to be patent at time=T2, reduce the pressure at the puncture site of the radial artery provided there is no bleeding. Also, at time=T2, reduce the pressure on the ulnar artery to make the ulnar artery partially compressed irrespective of whether the radial artery is patent or not patent. In one embodiment, T1 is about 15 minutes and T2 is about 30 minutes. Continue compression of radial artery until hemostasis at the puncture site. In one embodiment, continue partial compression of ulnar artery at least until hemostasis of the radial artery. In another embodiment, reduce the pressure on the ulnar artery to zero before hemostasis of the radial artery. In another embodiment, reduce the pressure on the ulnar artery to zero at T2=15 minutes. In yet another embodiment, reduce the pressure on the ulnar artery to zero at T2=30 minutes. In one embodiment T1 is half of T2.

Figure 17:
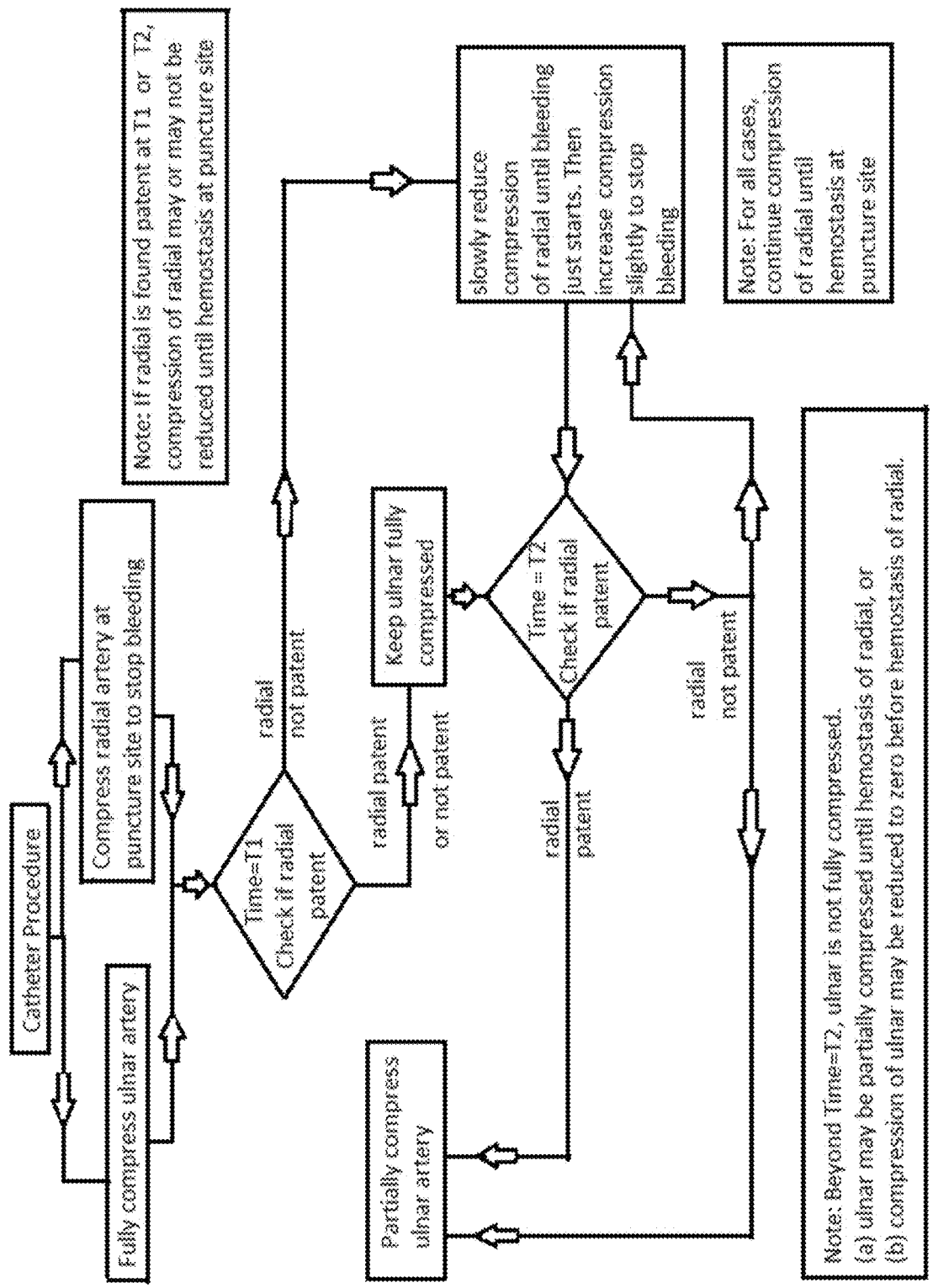
FIG. 17 is a schematic diagram of an embodiment of the invention depicting the steps to obtain patent hemostasis of the radial artery by compressing the ulnar artery.

In another embodiment as shown in FIG. 17, after completing the catheterization procedure, pressure is applied to ulnar artery to fully compress the ulnar artery and pressure is applied to the puncture site of the radial artery to stop bleeding. In one embodiment, pressure is applied to the ulnar artery before the pressure is applied to the radial artery. In another embodiment, pressure is applied to the radial artery before the pressure is applied to the ulnar artery. At time=T1 from the time ulnar artery was fully compressed, check whether the radial artery is patent. If the radial artery is not found to be patent at time=T1, reduce the pressure at the puncture site of the radial artery provided there is no bleeding. Continue full compression of ulnar artery. Check again the patency of radial artery at time=T2. If the radial artery is not found to be patent at time=T2, further reduce the pressure at the puncture site of the radial artery provided there is no bleeding. Also, at time=T2, reduce the pressure on the ulnar artery to make the ulnar artery partially compressed irrespective of whether the radial artery is patent or not patent. In one embodiment, T1 is about 15 minutes and T2 is about 30 minutes. Continue compression of radial artery until hemostasis at the puncture site. In one embodiment, continue partial compression of ulnar artery at least until hemostasis of the radial artery. In another embodiment, reduce the pressure on the ulnar artery to zero before hemostasis of the radial artery. In another embodiment, reduce the pressure on the ulnar artery to zero at T2=15 minutes. In yet another embodiment, reduce the pressure on the ulnar artery to zero at T2=30 minutes. In one embodiment T1 is half of T2.

Figure 18:
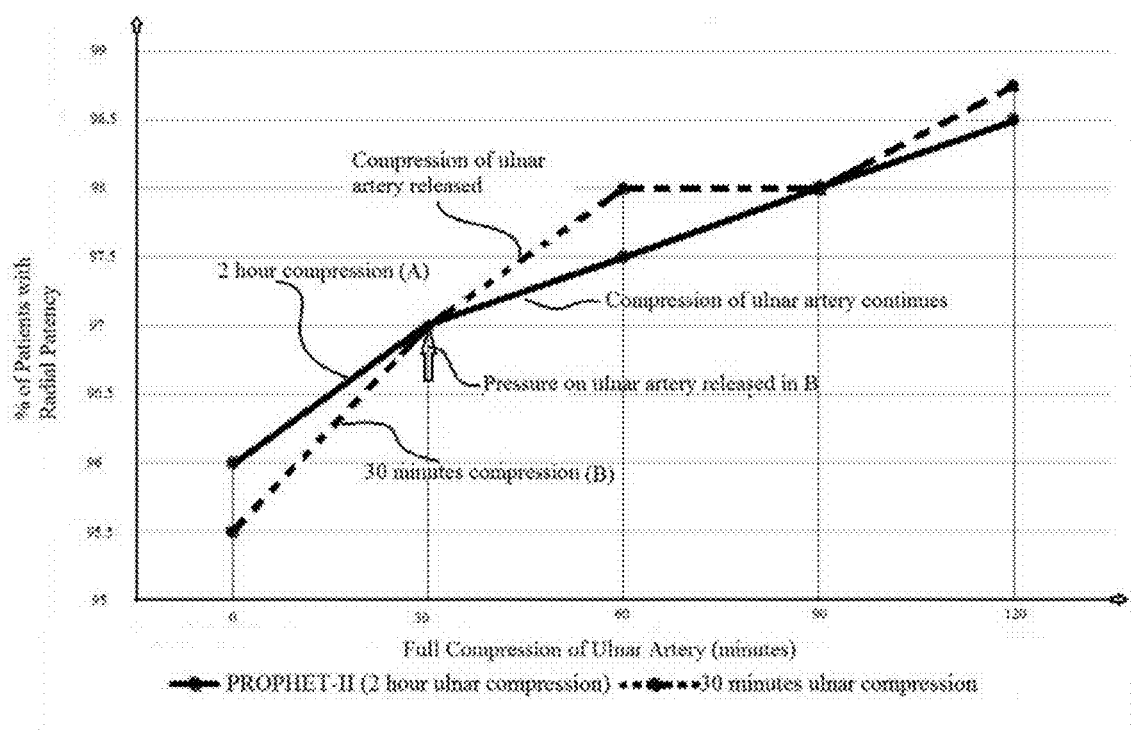
FIG. 18 is a graph showing comparative findings of radial artery patency.

FIG. 18 shows comparative findings of radial artery patency using a protocol compressing ipsilateral ulnar artery completely to the point of verified occlusion for a duration of 2 hours (PROPHET-II protocol) versus compression of ipsilateral ulnar artery completely for the first 30 minutes of simultaneous instrumented radial artery compression, after which the ipsilateral ulnar artery compression was released. The x-axis of the graph in FIG. 18 is the time from onset of compression of the instrumented radial artery and ipsilateral ulnar artery. The y-axis of the graph in FIG. 18 is the percentage of patients with patency in the radial artery. The patency was tested every 30 minutes. The radial patency with either of these strategies was comparable at the completion of radial artery hemostatic compression at 2 hours.

It will be appreciated that several of the above-disclosed and other features and functions, or alternatives or varieties thereof, may be desirably combined into many other different methods, systems or applications. Also, that various alternatives, modifications, variations or improvements therein may be subsequently made by those skilled in the art which are also intended to be encompassed by the following claims.

In the description above, for the purposes of explanation, numerous specific requirements and several specific details have been set forth in order to provide an understanding of certain embodiments. It will be apparent however, to one skilled in the art, that one or more other embodiments may be practiced without one or more of these specific details. The particular embodiments described are not provided to limit the invention, but to illustrate it. The scope of the invention is not to be determined by the specific examples provided above. In other instances, well-known structures, devices, and operations have been shown in block diagram form or without detail in order to avoid obscuring the understanding of the description. Where considered appropriate, reference numerals or terminal portions of reference numerals have been repeated among the figures to indicate corresponding or analogous elements, which may optionally have similar characteristics.

It should also be appreciated that reference throughout this specification to "one embodiment", "an embodiment", "one or more embodiments", or "different embodiments", for example, means that a particular feature may be included in the practice of the invention. Similarly, it should be appreciated that in the description various features are sometimes grouped together in a single embodiment, figure, or description thereof to streamlining the disclosure and aiding in the understanding of various inventive aspects. This method of disclosure, however, is not to be interpreted or construed as reflecting an intention that the invention requires more features than are expressly recited in each claim. Rather, as the following claims reflect, inventive aspects may lie in less than all features of a single disclosed embodiment. In another situation, an inventive aspect may include a combination of embodiments described herein or in a combination of less than all aspects described in a combination of embodiments.

The invention claimed is:

1. A method of attaining hemostasis of a radial artery of a patient after performing a catheterization procedure at an access site on the radial artery, comprising performing the following steps:
   (a) applying a radial pressure on the radial artery by inflating at least a first bladder to stop bleeding at the access site;
   (b) applying an ulnar pressure on an ulnar artery by inflating at least a second bladder at an ulnar pressure site;
   (c) continuing to apply the radial pressure on the radial artery for a duration of time to attain hemostasis of the radial artery;
   (d) continuing to apply the ulnar pressure on the ulnar artery at the ulnar pressure site to compress the ulnar artery fully for a first period of time, wherein the first period of time is at least 15 minutes; and
   (e) attaining hemostasis of the radial artery;
   wherein the first period of time is less than the duration of time to attain hemostasis of the radial artery, whereby the ulnar pressure is reduced to zero for a second period of time up until and including the moment in which hemostasis of the radial artery is attained.

2. The method of claim 1, wherein step (b) precedes step (a).

3. The method of claim 1, wherein an introducer sheath used in the catheterization procedure is removed after step (b).

4. The method of claim 1, further comprising a step of confirming patency of the radial artery.

5. The method of claim 1, wherein the ulnar pressure site is a Guyon's canal.

6. The method of claim 1, further comprising administering a dose of an anticoagulant at any time before introduction of a catheter or an introducer sheath, or administering the anticoagulant at any time after introduction of a catheter or an introducer sheath and before removal of the catheter or the introducer sheath.

7. The method of claim 6, wherein the anticoagulant is selected from a group consisting of: heparin, dalteparin, danaparoid, enoxaparin, unfractionated heparin, low molecular weight heparin, direct thrombin inhibitors including hirudin, argatroban, bivalirudin, and combinations or derivatives thereof.

8. The method of claim 6, wherein the dose of the anticoagulant is less than an equivalent of about 50 units of unfractionated heparin per kg of body weight.

9. The method of claim 1, wherein the duration of time in step (c) is less than 120 minutes.

10. The method of claim 1, wherein the duration of time in step (c) is about 60 minutes.

11. The method of claim 1, wherein the first bladder and the second bladder are connected to a band.

12. The method of claim 1, further comprising a step of slowly reducing compression of the radial artery until bleeding just starts, and then increasing compression slightly to stop bleeding.

13. The method of claim 12, wherein the step of slowly reducing compression of the radial artery until bleeding just starts, and then increasing compression slightly to stop bleeding is performed after step (d).

14. A method of attaining hemostasis of a radial artery of a patient after performing a catheterization procedure at an access site on the radial artery, comprising performing the following steps:
   (a) applying a radial pressure on the radial artery by inflating at least a first bladder to stop bleeding at the access site;
   (b) applying an ulnar pressure on an ulnar artery by inflating at least a second bladder at an ulnar pressure site;
   (c) continuing to apply the radial pressure on the radial artery for a duration of time to attain hemostasis of the radial artery;
   (d) continuing to apply the ulnar pressure on the ulnar artery at the ulnar pressure site to compress the ulnar artery fully for a first period of time, wherein the first period of time is either about 15 minutes or about 30 minutes; and
   (e) attaining hemostasis of the radial artery;
   wherein the first period of time is less than the duration of time to attain hemostasis of the radial artery, whereby after the first period of time the ulnar pressure is reduced to zero for a second period of time up until and including the moment in which hemostasis of the radial artery is attained.

15. The method of claim 14, wherein the first bladder and the second bladder are connected to a band.

16. The method of claim 14, further comprising administering a dose of an anticoagulant at any time before introduction of a catheter or an introducer sheath, or administering the anticoagulant at any time after introduction of a catheter or an introducer sheath and before removal of the catheter or the introducer sheath, and the dose of the anticoagulant is less than an equivalent of about 50 units of unfractionated heparin per kg of body weight.

17. The method of claim 14, further comprising a step of slowly reducing compression of the radial artery until bleeding just starts, and then increasing compression slightly to stop bleeding.

18. The method of claim 14, wherein the duration of time in step (c) is less than 120 minutes.

* * * * *